(12) United States Patent
Orfield et al.

(10) Patent No.: US 9,719,897 B2
(45) Date of Patent: *Aug. 1, 2017

(54) SYSTEM AND METHOD FOR BIOLOGICAL SPECIMEN MOUNTING

(71) Applicant: Alessi Technologies, LLC, Ann Arbor, MI (US)

(72) Inventors: Nolan Orfield, Ann Arbor, MI (US); Collin Rich, Ann Arbor, MI (US); Vincent Alessi, Ann Arbor, MI (US)

(73) Assignee: Alessi Technologies, LLC, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/131,993

(22) Filed: Apr. 18, 2016

(65) Prior Publication Data

US 2016/0231206 A1 Aug. 11, 2016

Related U.S. Application Data

(63) Continuation of application No. 14/706,479, filed on May 7, 2015, now Pat. No. 9,341,548, which is a continuation of application No. 14/574,210, filed on Dec. 17, 2014, now Pat. No. 9,041,922, application No. 15/131,993, filed on Apr. 18, 2016, which is a continuation of application No. 14/574,217, filed on Dec. 17, 2014, now Pat. No. 9,057,671.

(Continued)

(51) Int. Cl.
*G01N 21/01* (2006.01)
*G01N 1/28* (2006.01)
*G01N 1/31* (2006.01)
*G01N 1/44* (2006.01)
*G01N 1/06* (2006.01)
*G01N 35/00* (2006.01)

(52) U.S. Cl.
CPC ............... *G01N 1/312* (2013.01); *G01N 1/06* (2013.01); *G01N 1/2813* (2013.01); *G01N 1/44* (2013.01); *G01N 35/00029* (2013.01); *G01N 35/00871* (2013.01); *G01N 2035/00039* (2013.01); *G01N 2035/00138* (2013.01)

(58) Field of Classification Search
CPC   G01N 1/06; G01N 1/08; G01N 1/312; G01N 2035/00138
USPC ...... 356/244, 246, 440; 435/40.52; 382/128; 600/476

See application file for complete search history.

(56) References Cited

U.S. PATENT DOCUMENTS 3,552,247 A    1/1971  Pickett
4,120,991 A   10/1978  Ornstein et al.
(Continued)

*Primary Examiner* — Hoa Pham
(74) *Attorney, Agent, or Firm* — Jeffrey Schox; Ivan Wong

(57) ABSTRACT

A system and method for mounting a section onto a substrate, the system comprising: a fluid channel including: a fluid channel inlet that receives the section, processed from a bulk embedded sample by a sample sectioning module positioned proximal the fluid channel inlet, a section-mounting region downstream of the fluid channel inlet, and a fluid channel outlet downstream of the section-mounting region; a reservoir in fluid communication with the fluid channel outlet; and a manifold, fluidly coupled to the reservoir, that delivers fluid from the reservoir to the fluid channel inlet, thereby transmitting fluid flow that drives delivery of the section from the fluid channel inlet toward the section-mounting region.

20 Claims, 24 Drawing Sheets

Related U.S. Application Data

(60) Provisional application No. 61/917,219, filed on Dec. 17, 2013, provisional application No. 62/034,935, filed on Aug. 8, 2014.

(56) References Cited

U.S. PATENT DOCUMENTS

| | | |
|---|---|---|
| 4,985,206 A | 1/1991 | Bowman et al. |
| 5,713,255 A | 2/1998 | Izvozichikov et al. |
| 7,217,392 B2 | 5/2007 | Bogen et al. |
| 7,270,785 B1 | 9/2007 | Lemme et al. |
| 7,277,166 B2 | 10/2007 | Padmanabhan et al. |
| 8,245,613 B2 | 8/2012 | Miyatani et al. |
| 8,366,857 B2 | 2/2013 | Hayworth et al. |
| 8,734,735 B2 | 5/2014 | Williamson et al. |
| 8,771,978 B2 | 7/2014 | Ragan |
| 8,778,630 B2 | 7/2014 | Iyer et al. |
| 9,041,922 B1 * | 5/2015 | Orfield .............. G01N 1/2813 356/244 |
| 9,057,671 B1 * | 6/2015 | Orfield .............. G01N 1/2813 |
| 9,341,548 B2 * | 5/2016 | Orfield .............. G01N 1/2813 |
| 2007/0204740 A1 | 9/2007 | Miyatani et al. |
| 2007/0257215 A1 | 11/2007 | Rich |
| 2009/0074625 A1 | 3/2009 | Johnson et al. |
| 2009/0215112 A1 | 8/2009 | Iyer et al. |
| 2010/0000383 A1 * | 1/2010 | Koos ................. G01N 1/06 83/22 |
| 2010/0210008 A1 | 8/2010 | Strand et al. |
| 2011/0299157 A1 | 12/2011 | Alessi |
| 2011/0299158 A1 | 12/2011 | Alessi |
| 2012/0088267 A1 | 4/2012 | Iyer et al. |
| 2012/0208184 A1 * | 8/2012 | Ragan ............... G01N 1/06 435/6.11 |
| 2013/0019725 A1 * | 1/2013 | Magavi ............. G01N 1/06 83/24 |
| 2013/0216451 A1 | 8/2013 | Hayworth et al. |
| 2014/0026683 A1 | 1/2014 | Hayworth et al. |
| 2014/0255986 A1 | 9/2014 | Williamson et al. |
| 2015/0223646 A1 | 8/2015 | Wegelin et al. |

* cited by examiner

High flow rate
-Bend and Separate Sections

Low flow rate
-Cushion for no-crumple cutting forms

CROSS SECTION

CROSS SECTION

CROSS SECTION

Phase 1: Section Delivery
Flow active, with substrate submerged

Phase 2: Section Placement
Flow off/reduced, then substrate is retracted

Phase 3: Waste Discarded
Flow active with substrate retracted

SYSTEM AND METHOD FOR BIOLOGICAL SPECIMEN MOUNTING

CROSS-REFERENCE TO RELATED APPLICATIONS

This application is a continuation of co-pending U.S. patent application Ser. No. 14/706,479, filed 7 May 2015, which is a continuation of U.S. patent application Ser. No. 14/574,210, filed 17 Dec. 2014, now issued as U.S. Pat. No. 9,041,922, which claims the benefit of U.S. Provisional Application Ser. No. 61/917,219, filed 17 Dec. 2013 and U.S. Provisional Application Ser. No. 62/034,935, filed 8 Aug. 2014, which are each incorporated in its entirety herein by this reference. This application is also a continuation of co-pending U.S. patent application Ser. No. 14/706,479, filed 7 May 2015, which is a continuation of U.S. patent application Ser. No. 14/574,217, filed 17 Dec. 2014, now issued as U.S. Pat. No. 9,057,671, the entirety of which is incorporated herein by this reference.

TECHNICAL FIELD

This invention relates generally to the biological research field, and more specifically to a new system and method biological specimen mounting.

BACKGROUND

It is commonly desirable in biological laboratories to mount tissue sections, or 'specimens', to slides for purposes of examining the tissue sections using a microscope, treating the tissue sections with a stain or dye, and for other purposes. As shown in FIG. 1, conventional systems and methods for mounting specimens onto slides comprise placing tissue sections in a sufficiently deep water bath, with the specimens floating on the surface of the water. The broad side of a slide is then rested on the rim of the water bath and the slide is angled down into the water back such that the slide is partially submersed in the water. Subsequently, a small brush or glass capillary tube is used to manipulate a tissue section onto the slide. Typically, the slide is gradually drawn out of the water as additional tissue sections are arranged on the slide. In another variation of a conventional method, tissue is embedded in paraffin wax, sliced with a microtome, and then selected sections of the embedded tissue are transferred to a heated water bath. The hot water bath partially melts the paraffin about the specimens, and a glass slide treated with adherents is then used to scoop the tissue sections out of the hot water bath. Conventional methods of mounting specimens on slides are thus difficult, time-consuming, and labor-intensive.

There is thus a need in the biological research field for a new system and method for biological specimen mounting. This invention provides such a new system and method.

DESCRIPTION OF THE EMBODIMENTS

The following description of preferred embodiments of the invention is not intended to limit the invention to these embodiments, but rather to enable any person skilled in the art to make and use this invention.

1. System

Figure 1:
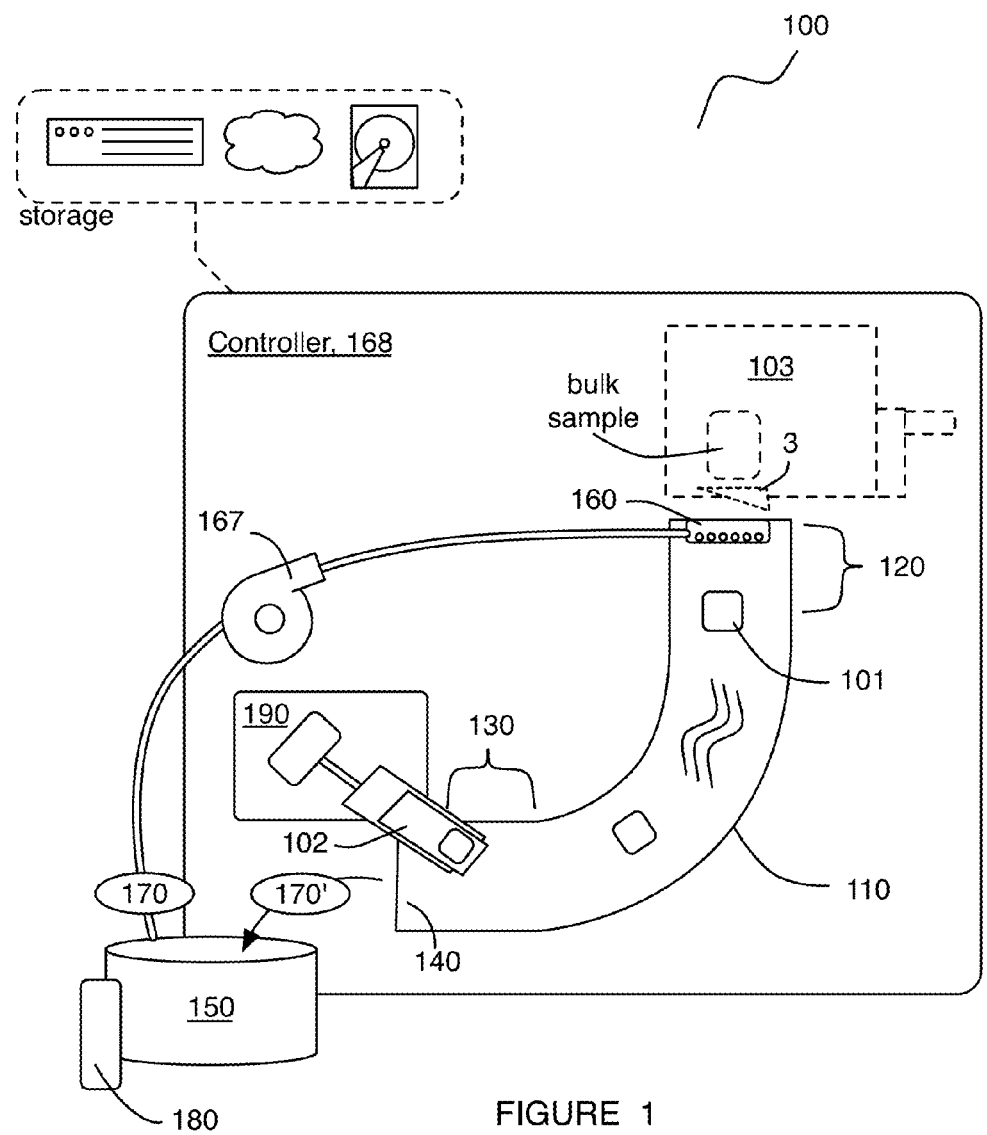
FIG. 1 depicts a schematic of an embodiment of a system for mounting a section to a substrate.

As shown in FIG. 1, an embodiment of a system 100 for coupling a section 101 to a substrate 102 comprises: a fluid channel 110 having a fluid channel inlet 120 that receives the section 101, processed from a bulk embedded sample by a sample sectioning module 103 positioned proximal the fluid channel inlet 120, a section-mounting region 130 downstream of the fluid channel inlet, and a fluid channel outlet 140 downstream of the section-mounting region; a reservoir 150 in fluid communication with the fluid channel outlet; and a manifold 160 fluidly coupled to the reservoir, that delivers fluid from the reservoir to the fluid channel inlet, thereby transmitting fluid flow that drives delivery of the section from the fluid channel inlet toward the section-mounting reservoir. In some embodiments, the system 100 can additionally or alternatively include any one or more of: a filter 170, fluidly configured between the fluid channel outlet and the manifold, that prevents undesired substances from flowing into the fluid channel inlet; a temperature regulating module 180 in contact with fluid from the reservoir, that adjusts a temperature of fluid within the fluid channel; and a substrate actuation module 190 that transmits the substrate into the section-mounting region in a first operation, and delivers the substrate from the section-mounting region, with the section mounted to the substrate, in a second operation.

The system 100 functions to automate processing of sections (e.g., histological specimen sections, biological sections, etc.) in a manner that consistently generates high-quality mounted sections, with minimal or no effort from a human technician. As such, the system 100 can significantly reduce labor-intensive aspects of mounting sections to substrates. The system 100 is preferably configured to implement at least a portion of the method 200 described in Section 2 below.

In one specific workflow, the system 100 is configured to retrieve a thin tissue section (e.g., generated from a microtome blade), to separate the tissue section from a preceding section, to transport the section to a microscope slide via a fluidic channel, and then to mount the section onto the microscope slide with a substrate actuation module that coordinates movement of the microscope slide in relation to motion of the tissue section within the fluidic channel. In mounting a tissue section onto the microscope slide, the geometry of the fluidic channel is configured to deliver the tissue section toward an interface at which the microscope slide and the surface of fluid within the fluidic channel intersect, center the tissue section onto the microscope slide, and orient the tissue section such that its sides are parallel to long edges of the microscope slide. Mounting, in the specific workflow, is then consummated by causing a line of juncture between the microscope slide and the surface of the fluid within the fluidic channel to recede in a direction opposite to that of flow within the fluid section. In variations of the specific workflow, recession of the line of juncture to facilitate mounting can be accomplished by slowing flow of fluid (e.g., by decreasing a volumetric flow rate of fluid) within the fluidic channel, by providing relative motion between the fluidic channel and the microscope slide in a manner that enhances mounting of the tissue section to the microscope slide, by removing a previously-submerged displacing body from a fluid volume within the fluidic channel (i.e., to lower the fluid level within the fluid channel), and/or by any other suitable mechanism. In the specific workflow, the substrate actuation module can further be configured to modulate motion of the microscope slide to be positioned for placement of multiple sections onto the slide or to be fully retracted to create an unobstructed path to carry discarded sections to a reservoir for filtration and/or recirculation. The system 100 can, however, facilitate any other suitable workflow or method involving any other suitable section and/or imaging substrate.

Figure 2:
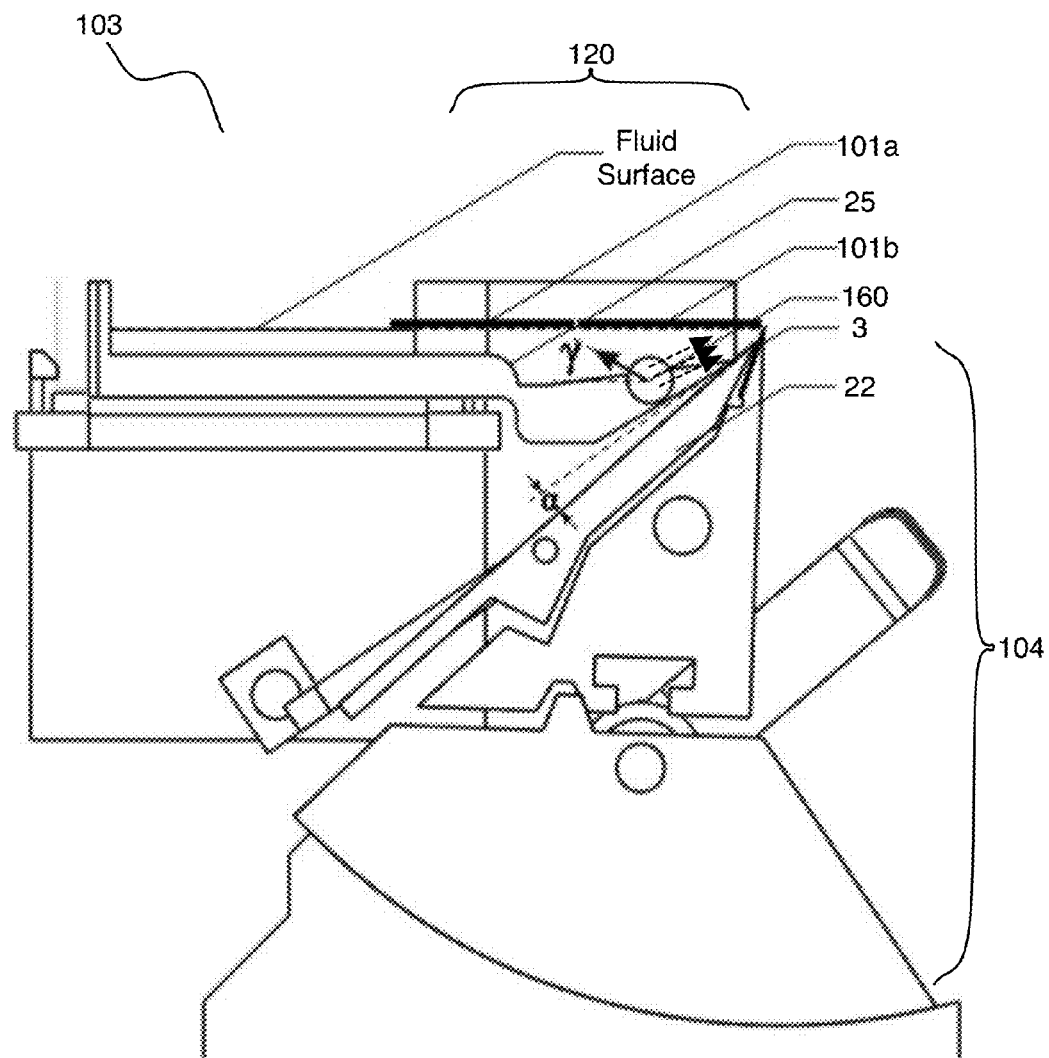
FIG. 2 depicts an example of a sample sectioning module interfacing with a system for mounting a section to a substrate.

In variations wherein the system 100 interacts or integrates with a sample sectioning module 103, the system 100 can be configured to cooperate with the sample sectioning module 103 in order to separate serially connected sections generated by the sample sectioning module 103 for transmission into the fluid channel 110. In one example of a sample sectioning module 103 comprising a microtome 104, as shown in FIG. 2, a blade 3 (e.g., microtome blade) of the microtome 104 is retained in position by a blade holder having a stage 22 that collects tissue sections during normal operation. The microtome 104 can have an adjustable blade angle and an adjustable stage angle $\alpha$, as shown in FIG. 2, that coordinates with an angle of the blade. The stage 22 of the microtome 104 can thus rotate with an axis of rotation about the tip of the blade 3, and the system 100 can mate with the stage 22 along an interface (e.g., linear interface) between the blade 3 and the system 100 such that the blade angle can be adjusted without repositioning of the system 100. Furthermore, this configuration allows for lateral adjustment of the blade 3 within the microtome, without repositioning of the system 100 in relation to the microtome 104. The system 100 can further be hermetically sealed against the stage 22 at the fluid channel 110 or manifold 160 (e.g., using a sealing gasket, using mechanical pressure, etc.) in order to minimize fluid leakage at an interface between the stage 22 and the fluidic channel 110. In one alternative to the specific example, the system 100 can directly interface with the stage 22 or another portion of the blade-holding portions of the microtome 104. In another alternative to the specific example, the system 100 can include portions that substitute for the stage 22 and couple directly to blade-holding portions of the microtome 104. The sample sectioning module 103 can, however, include any other suitable elements or be configured relative to the system 100 in any other suitable manner.

In the example above, each cut motion of the microtome 104 produces a new section 101, and the embedding material used for the section 101 preferably has a density lower than that of fluid (e.g., water) flowing through the system 100, such that the section 100 floats on the surface of the fluid. Preferably, each generated section 101 remains coupled to the blade 3 (e.g., loosely coupled to the blade by way of the embedding medium), and fluid introduced through a manifold 160 into the fluid channel 110 at an angle $\gamma$ frees a preceding section for transmission through the fluid channel 110 and mounting. Flow at the angle $\gamma$ frees the preceding section by providing a force that produces tension at a junction between serial sections generated at the microtome 104. Additionally, in a related example, a portion of fluid flow from the manifold 160 is directed to flow against the stage 22 and in a superior direction towards the blade 3, which facilitates uniform pulling of sections away from the blade 3 as they are cut by the blade 3. Furthermore, in the related example, features (i.e., fins) oriented with a direction of fluid flow within the fluid channel 110 at the fluid channel inlet 120 promote laminar flow away from the blade 3.

Figure 3A:
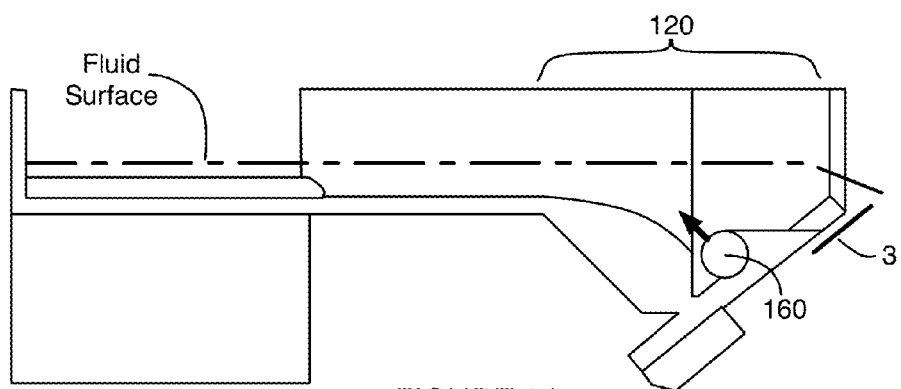
FIGS. 3A-3C depict variations of a portion of a fluid channel in an embodiment of a system for mounting a section to a substrate.
Figure 3B:
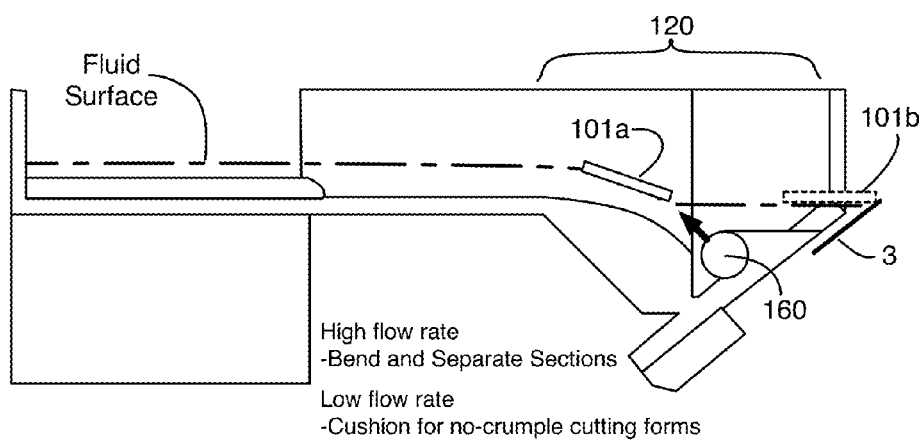
Figure 3C:
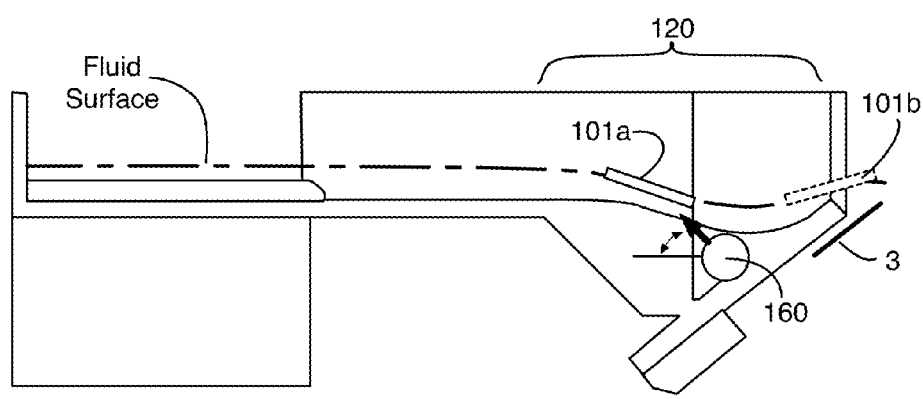

Additionally or alternatively, separation of a section 101 from the blade 3 can be performed by generating fluid flow beneath a section 101 within the fluid channel 110, such that a shear force induced at a junction between sections provides separation. Still alternatively, an operator can manually separate a section 101 from the blade 3 (e.g., using forceps). Still alternatively, an elevated floor of the fluid channel inlet 120, immediately downstream of the manifold 160, can cause fluid to be drawn away from the blade 3 as it is delivered into the fluid channel 100. Such a configuration, as shown in FIGS. 3A and 3B, enables a cushion of water to develop near the blade 3 with high flow rates, and can allow multiple sections to be separated using flow speed modulations that retain a section attached to the blade 3, while biasing a preceding section away from the blade 3. Still alternatively, as shown in FIG. 3C, a concave surface 111 of the fluid channel inlet 120 can provide a "bowl" of fluid that facilitates retention of a section attached to the microtome blade 3, while openings of the manifold 160 project fluid underneath the section to facilitate separation of adjoining sections. Multiple orifice angles, as shown in FIG. 3C, can provide a force that facilitates flexing of adjoining sections, thereby promoting separation from a shear force induced at a junction between adjoining sections.

Figure 4A:
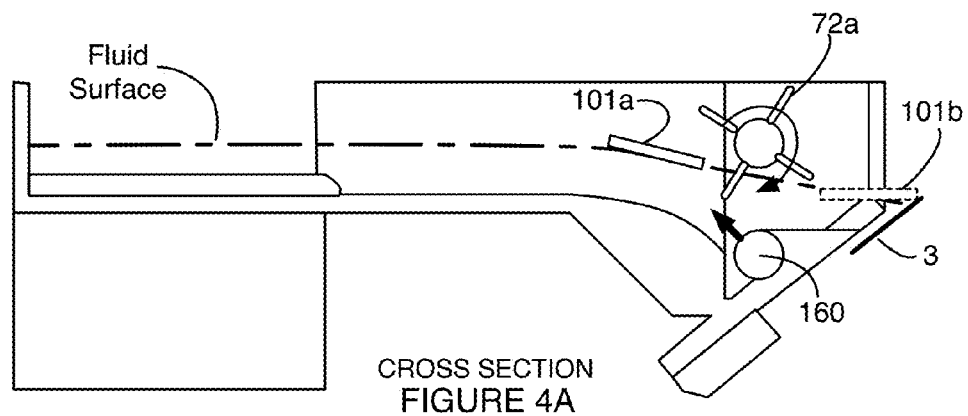
FIGS. 4A-4C depict variations of elements configured to separate adjoining sections in an embodiment of a system for mounting a section to a substrate.
Figure 4B:
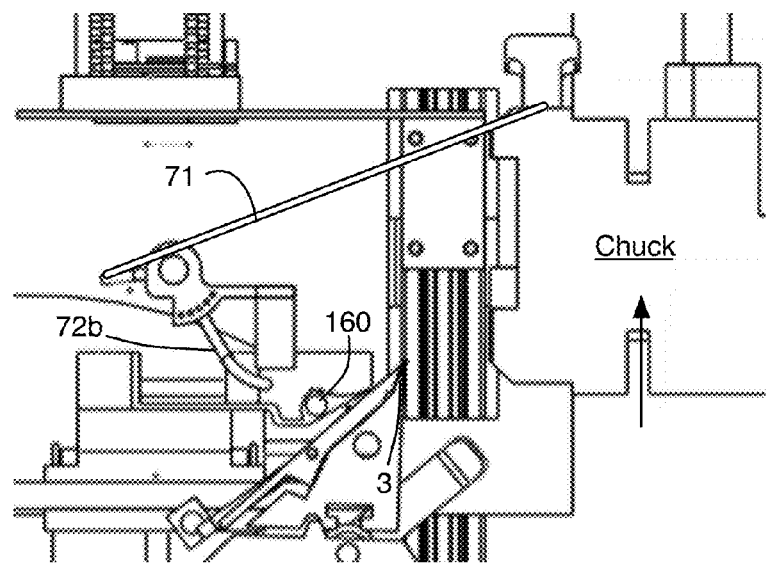
Figure 4C:
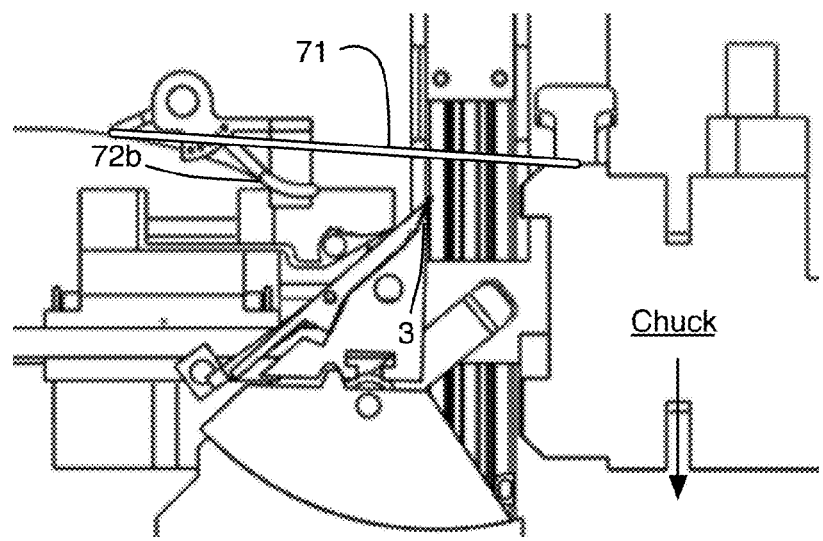

Still alternatively, a separation device of the system 100 (e.g., a paddle, a chuck, a solenoid plunger, etc.) can use mechanical force to separate adjoined sections. In one example, as shown in FIG. 4A, fluid flow can modulate motion of a separation device 72a in separating adjoined sections and allowing a released section to be transmitted into downstream portions of the fluidic channel 110. In another example with a paddle 72b, as shown in FIG. 4B, as the microtome chuck rises, a band 71 connecting a lever arm on the paddle 72b to the chuck can pass above the paddle's pivot point, causing the paddle to transition to an active configuration. Then, the paddle 72b can be configured to revert to an inactive configuration, as shown in FIG. 4C, when the chuck descends as sections are being sliced from the bulk embedded sample. In yet another example, a solenoid plunger configured proximal the fluid channel inlet 120 can provide a force that separates a section from an adjoining section.

Once a section 101 has been separated in any of the above variations and examples, a shallower depth 25 within the fluid channel 110, as described in further detail below, can allow the section 101 to accelerate toward downstream portions of the fluid channel 110. In any of the above examples, having a section 101 adhere to the blade 3 for a brief period of time prior to separation by fluid transmission allows an operator to observe its quality and intervene in the sample processing process, if necessary. Floating a section 101 atop fluid in the fluid channel 110, with coupling of the section 101 to the blade 3 can further function to reduce the presence of any wrinkling in the section 101. Additionally or alternatively, in any of the examples, 1.1 System—Fluid Channel The fluid channel 110 has a fluid channel inlet 120 that receives the section 101, processed from a bulk embedded sample by a sample sectioning module 103 positioned proximal the fluid channel inlet 120, a section-mounting region 130 downstream of the fluid channel inlet, and a fluid channel outlet 140 downstream of the section-mounting region. The fluid channel 110 functions to receive the section 101 from a sample sectioning module 103, and to deliver the section over a layer of flowing fluid that drives the section for mounting at a downstream position. The fluid channel 110 preferably defines a primarily straight flow path; however, in some variations, the fluid channel 110 can alternatively define a curved flow path or any other suitable flow path. Preferably, the fluid channel 110 is wider than a maximum width of the section in order to facilitate smooth transmission of the section into the fluid channel 110 (e.g., to prevent jamming) during delivery along the fluid channel 110. However, the fluid channel can alternatively have any other suitable width relative to a width of the section. Furthermore, the width and/or depth of the fluid channel 110 can be constant or variable, in order to produce desired flow behavior through portions of the fluid channel 110. As such, constricted portions of the fluid channel 110 can produce higher velocities of fluid flow than less constricted portions of the fluid channel 110, given a volumetric flow rate of fluid through the fluid channel 110. In some variations, the fluid channel 110 can have at least one declined portion relative to a horizontal plane in order to passively facilitate fluid flow. In some variations, the fluid channel 110 can additionally or alternatively comprise portions that are flat or inclined relative to a horizontal plane.

Figure 5:
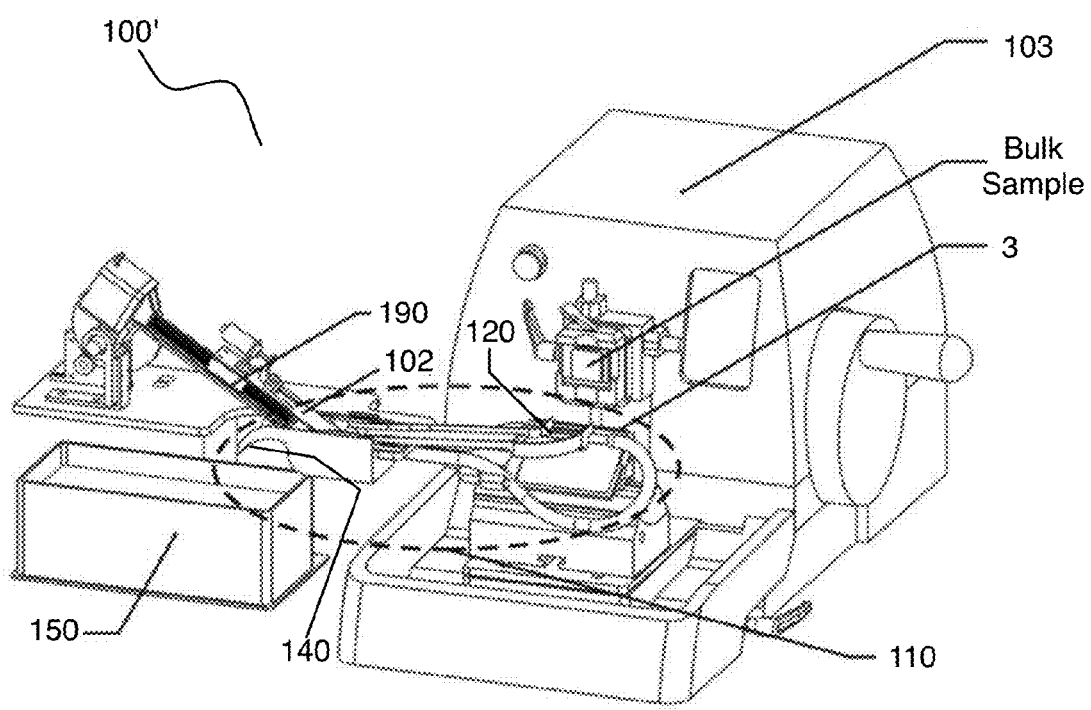
FIG. 5 depicts an example of a system for mounting a section to a substrate.

The fluid channel inlet 120 is preferably configured proximal to an output region of the sample sectioning module 103, in order to facilitate initial positioning of the section, from the sample sectioning module 103, within the fluid channel inlet 120. In specific examples, as shown in FIGS. 2 and 5, the fluid channel inlet 120 is configured proximal to a blade 3 (e.g., a stationary blade) of a microtome, wherein interaction between a bulk embedded sample (i.e., a biological sample embedded in wax) and the blade generates the section and delivers the section toward the fluid channel inlet 120. In the specific example, the bulk embedded sample is configured to couple to an actuator that moves the bulk embedded sample relative to the stationary blade to generate sections; however, variations of the specific example can involve any other suitable relative motion between a bulk embedded sample and a cutting instrument to generate sections. As such, the system 100 can be configured to couple directly to or to be positioned adjacent to an output region of a sample sectioning module 103; however, the system 100 can additionally or alternatively be configured such that a user or other entity can transfer a section generated from any suitable sectioning device to the fluid channel inlet 120 for histological mounting.

The fluid channel inlet 120 preferably has a width substantially larger than that of a section 101 generated from a bulk embedded sample, in order to prevent wrinkling or any other form of damage to the section 101 upon transmission into the fluid channel inlet 120. In variations, the fluid channel inlet 120 can have a width that is from 115% to 300% of the width of a section 101 generated by the sample sectioning module 103. However, the width of the fluid channel inlet 120 can alternatively be any other suitable size in relation to a width of a sample generated at the sample sectioning module 103. Furthermore, the width of the fluid channel 110 can be modulated from the fluid channel inlet 120, to the section-mounting region 130, to the fluid channel outlet 140, in order to facilitate focusing and/or accurate positioning of a section 101 onto a substrate 102 at the section-mounting region 130; however, the width of the fluid channel 110 can alternatively be substantially constant across two or more of the fluid channel inlet 120, the section-mounting region 130, and the fluid channel outlet 140.

Figure 6A:
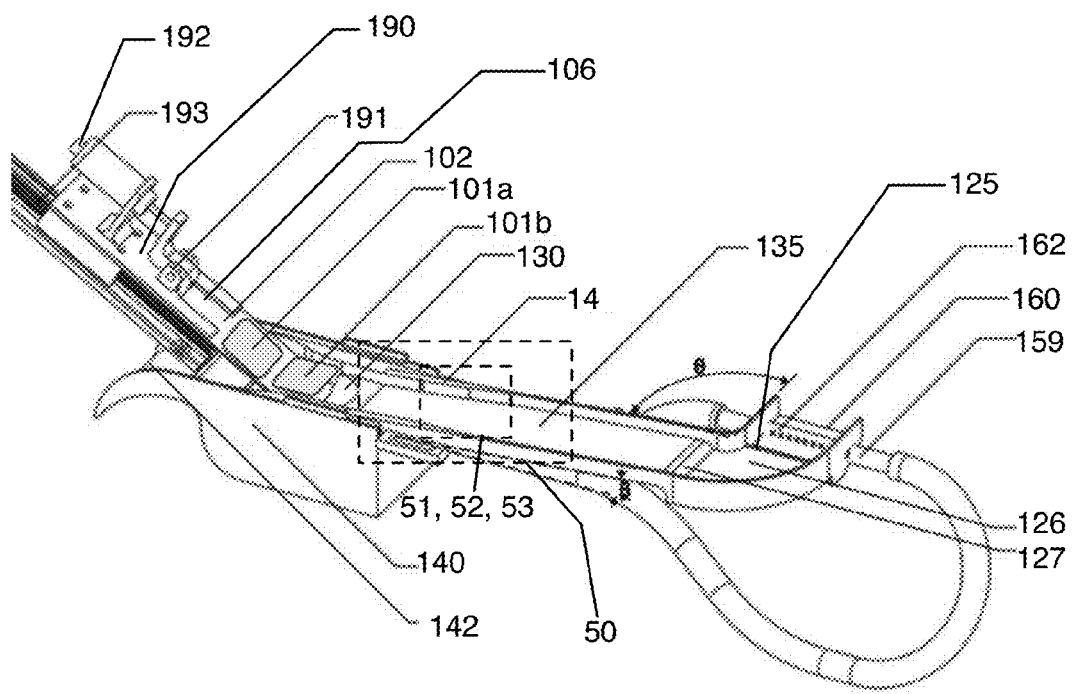
FIG. 6A depicts an example of a portion of a system for mounting a section to a substrate.

In some variations, the fluid channel inlet 120 can comprise a junction 125 at an upstream portion of the fluid channel inlet 120, as shown in FIG. 6A, such that the junction 125 diverts a direction of fluid flow into the fluid channel 100. As such, the junction 125 can function to provide a more compact and non-interfering interface between the fluid channel 110 and the sample sectioning module 103. In one example, the junction is a 90° junction that allows a section transmitted into the fluid channel 110 to be diverted by an angle of approximately 90° between the sample sectioning module 103 and the fluid channel inlet 120. Such a configuration facilitates positioning of the system 100 to interface with the sample sectioning module 103 in a first configuration (e.g., a coupled configuration), and facilitates removal of the system 100 from interfacing with the sample sectioning module 103 in a second configuration (e.g., a decoupled configuration). However, in alternative variations of the example, an angle of rotation between the fluid channel inlet 120 and the sample sectioning module 103, provided by the junction 125 and defined in FIG. 6A as θ, can alternatively range from 45° to 315°, or can have any other suitable angle depending upon morphological parameters of the fluid channel 110 and/or the sample sectioning module 103.

Figure 6B:
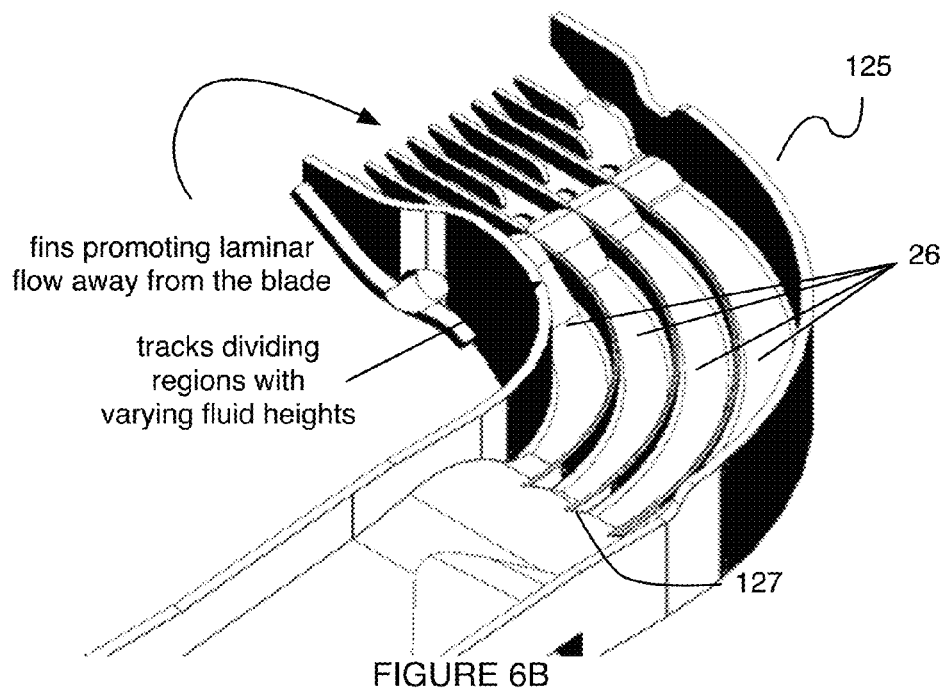
FIG. 6B depicts a portion of an example of a system for mounting a section to a substrate.

In some variations, the junction 125 can define a region with a raised floor 126, in relation to a manifold 160, as described in further detail below. The raised floor 126 functions to provide concentration of fluid flow into the fluid channel inlet 120, which allows acceleration of a section 101 floating atop and/or carried by fluid within the region of the junction 125 having a raised floor 126. As such, the raised floor 126 can provide an inlet reservoir that provides desired initial motion characteristics (e.g., velocity, acceleration, flow path, etc.) of a section 101 entering the fluid channel 110. Additionally or alternatively, the junction 125 can define a region that enables concentration of fluid flow into the fluid channel inlet 120 by defining a constricted cross-sectional area, perpendicular to a direction of fluid flow in the fluid channel inlet 120, in any other suitable manner. For instance, a width and/or depth of a region of the junction 125 can be decreased within the junction 125, relative to other portions of the fluidic channel 110, thereby concentrating fluid flow into the fluid channel inlet 120 and accelerating motion of a section 101 within the junction 125 for a given volumetric flow rate in the junction. In related variations, a curved region of the junction 125 of the fluid channel inlet 120 (e.g., the raised floor region 126) can include a set of tracks 26, a specific example of which is shown in FIG. 6B, wherein the set of tracks divide the curved region of the junction 125 into a set of regions with varying fluid heights. The set of tracks 26 thus allow fluid travelling along the outside of the curved region of the junction 125 (e.g., fluid travelling the greatest distance) to move faster, thereby fluidically rotating a section 101 as it rounds the curved region of the junction 125. This preserves an orientation of the section 101 (e.g., in relation to an orientation from the bulk embedded sample) and prevents jamming of sections within the system 100.

In some variations, an output region of the fluid channel inlet 120 (e.g., defined at an output region of the junction 125) can include a lip 127 (e.g., an elevated lip) protruding from a base surface of the fluid channel inlet 120/junction 125, that directs fluid, with a section 101, into portions of the fluid channel 110 downstream of the fluid channel inlet 120. The lip 127 can thus provide desired initial motion characteristics (e.g., velocity, acceleration, flow path, etc.) of a section 101 entering portions of fluid channel 110 downstream of the lip 127, such that sections travelling within the fluid channel 110 travel in a predictable and/or repeatable manner. The fluid channel inlet 120 and/or junction 125 can, however, include any other suitable features that provide predictable flow behavior (e.g., substantially constant streamlines) that drives motion of sections within the fluid channel 110.

Figure 8:
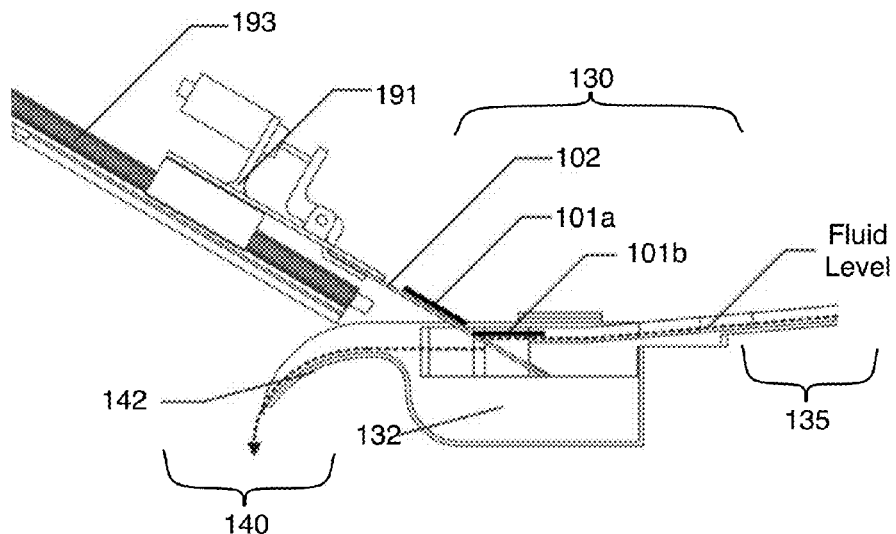
FIGS. 8 and 9 depict cross sectional views of variations of a portion of a system for mounting a section to a substrate.
Figure 9:
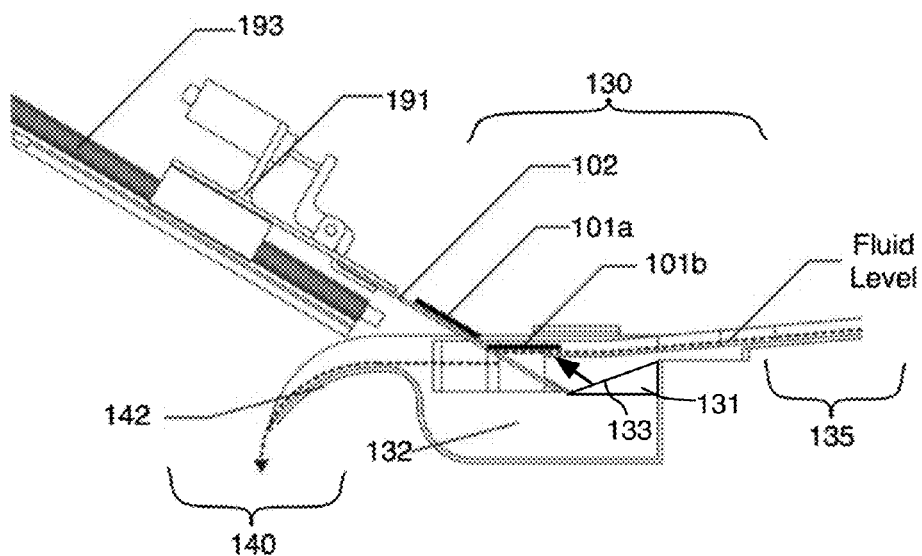

The section-mounting region 130 of the fluid channel 110 is preferably a region of the fluid channel 110 configured between the fluid channel inlet 120 and the fluid channel outlet 140, such that a section 101 transmitted into the fluid channel 110 by way of the sample sectioning module 103 is configured to be mounted to a substrate 102 at a region of the fluid channel 110 downstream of the fluid channel inlet 120 and upstream of the fluid channel outlet 140. Preferably, the section-mounting region 130 has a depth that can accommodate passage of an imaging substrate under a section (e.g., by way of the substrate actuation module 190) within the section-mounting region 130, without disturbance (e.g., wrinkling, damage) of the section. In an example, as shown in FIG. 8, the section-mounting region 130 comprises a section-mounting reservoir 132 that is substantially deeper than the depth of the fluid channel inlet 120 and that allows a substrate to be submerged to a sufficient depth below a section 101 that has been delivered into the section-mounting region 130. However, the section-mounting region 130 can alternatively be configured in any other suitable manner.

Preferably, the section-mounting region 130 is fluidly coupled to the fluid channel inlet 120 by a chute 135, as shown in FIG. 6A, that functions to transport sections from the fluid channel inlet 120 to the section-mounting region 130 in a predictable and repeatable manner. The chute 135 also functions to provide desired motion characteristics (e.g., velocity, acceleration, flow path, etc.) of a section 101 upon delivery into the section-mounting region 130, such that sequential sections travelling to the section-mounting region 130 reach the section-mounting region 130 in a consistent and desired manner. In one variation, the chute 135 can be oriented with a constant slope, defined in FIG. 6A as β, that provides downhill flow for acceleration of a section 101 from the fluid channel inlet 120 to the section-mounting region 130, as facilitated passively by gravitational force. Furthermore, in variations, the chute 135 can have an adjustable angle, such that the value of β can be adjusted (e.g., using an actuator coupled to the chute 135 or another portion of the fluidic channel 110). In specific examples, β has a value from 5-15°, and in variations of the specific examples, β can have a value from 0-60° to provide desired flow characteristics within the chute 135.

Alternatively, the chute 135 can have a varying slope along the length of the chute 135, from an upstream portion to a downstream portion of the chute 135, such that a profile of the chute 135 in an elevation view has a non-linear (e.g., curved) morphology. In one example, an upstream portion of the chute 135 has a steep slope (e.g., greater than 60°) relative to a horizontal plane, and the slope of the chute transitions to a substantially flat slope (e.g., less than 2°) in coupling to the section-mounting region 130.

The chute 135 preferably facilitates focusing and accurate positioning of a section 101 at the section-mounting region, by having a width dimension that is reduced (e.g., gradually reduced) from the fluid channel inlet 120 to the section-mounting region 130. In variations, the width of a downstream portion of the chute 135, proximal the section-mounting region 130, has a dimension that is from 105% to 125% of the width of a section 101 generated by the sample sectioning module 103, such that the width of the downstream portion of the chute is substantially reduced relative to the width of the fluid channel inlet 120. However, the width of the chute 135 can alternatively be any other suitable size in relation to a width of a sample generated at the sample sectioning module 103. Additionally or alternatively, accurate positioning of a section traveling along the chute 135 can be facilitated by generating one or more well-defined streamlines of fluid flow, using channel morphologies that provide hydrodynamic focusing. In one example, the chute 135 can define a curved path that enables hydrodynamic focusing of a section 101 to a well-defined position at the section-mounting region 130. In the example, the curved path can have a set of undulations that focus the section 101 from a not-well-defined position to a well-defined position in a consistent manner. Alternatively, a sonic steering module positioned at any portion of the fluid channel 110 can facilitate accurate positioning of a section. Still alternatively, accurate positioning of a section 101 at the section-mounting region 130 can be facilitated, by way of the chute 135, in any other suitable manner.

In some variations, the section-mounting region 130 can include a base surface having a geometric feature 131, as shown such that the geometric feature 131 is submerged below a fluid line of fluid within the fluid channel 110, and provides flow characteristics that facilitate mounting of a section 101 to a substrate 102 at the section-mounting region 130. In one such variation, the geometric feature 131 comprises a contoured surface 133 configured to align a section 101 passing over the geometric feature 131, by way of fluid flow into the section-mounting region 130, toward a desired position. In aligning the section 101, the contoured surface produces a force vector that biases the section 101 against a substrate 102 within the section-mounting region 130 and aligns the section 101 such that its sides are substantially parallel with long edges of the substrate 102. Alternatively, the section-mounting region 130 may omit a geometric feature 131 at a base surface, while still enabling mounting of a section 101 to a substrate 102 at the section-mounting region.

The fluid channel outlet 140 is preferably configured downstream of the section-mounting region 130, in order to provide an outlet for flow from the fluid channel 110. The fluid channel outlet 140 is preferably also configured to facilitate retrieval and/or filtration of undesired sections from the fluid channel 110. As such, in some variations, the fluid channel outlet 140 can be configured to couple to a filtration and recirculation module that allows fluid and undesired sections from the fluid channel 110 to be filtered of the undesired elements, while allowing recirculation of fluid throughout the system (e.g., by way of the reservoir 150). However, the fluid channel outlet 140 can alternatively be configured in any other suitable manner.

In one variation, an example of which is shown in FIGS. 6 and 8, the fluid channel outlet 140 comprises a curved spout 142 that allows fluid passing through the section-mounting region 130 to pass into a reservoir 150 that recirculates fluid back into the fluid channel 110. Alternatively, the fluid channel outlet 140 can have any other suitable morphology that allows fluid from the section-mounting region 130 to pass through the fluid channel outlet 140 and into the reservoir 150 for recirculation. For instance, the fluid channel outlet 140 can include one or more of: a non-curved spout, a funnel-shaped feature, a manifold, and any other suitable fluid guiding feature that allows fluid to be efficiently delivered into the reservoir 150 (e.g., without leakage, without loss). The fluid channel outlet 140 is preferably configured to receive fluid passing through the section-mounting region 130 and to deliver fluid into the reservoir 150 whether or not a substrate 102 is present within the section-mounting region 120; however, the fluid channel outlet 140 can alternatively be substantially obstructed when a substrate 102 is present within the section-mounting region 130. The fluid channel outlet 140 is preferably elevated relative to the reservoir 150, such that fluid from the fluid channel outlet 140 is passively delivered into the reservoir 150 as facilitated by gravity; however, the fluid channel outlet 140 can alternatively be configured relative to the reservoir in any other suitable orientation, wherein a driving element (e.g., pump) facilitates fluid flow from the fluid channel outlet 140 and into the reservoir 150.

Figure 7:
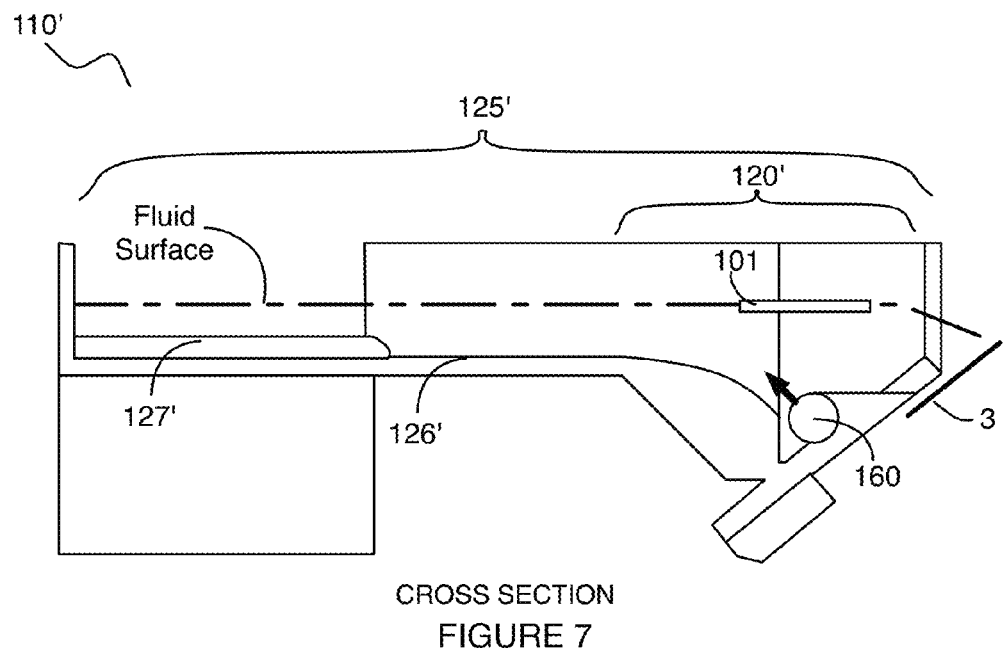
FIG. 7 depicts a variation of a junction in a fluid channel, in an embodiment of a system for mounting a section to a substrate.

In a specific example of the fluid channel 110', as shown in FIGS. 6B and 7, the fluid channel inlet 120' includes a junction 125' having a region with a raised floor 126', in relation to a manifold 160, that enables acceleration of a section 101 floating atop and/or carried by fluid within the fluid channel inlet 120'. In the specific example, a curved region of the junction 125, at the raised floor region 126, includes a set of tracks 26, wherein the set of tracks divide the curved region of the junction 125 into a set of regions with varying fluid heights, as shown in FIG. 6B. The set of tracks 26 in the specific example allow fluid travelling along the outside of the curved region of the junction 125 (e.g., fluid travelling the greatest distance) to move faster, thereby fluidically rotating a section 101 as it rounds the curved region of the junction 125. In the specific example, the fluid channel inlet 120' also includes an elevated lip 127' protruding from a base surface of the fluid channel inlet 125', that directs fluid, with a section 101, into portions of the fluid channel 110 downstream of the fluid channel inlet 120. In the specific example, the fluid channel 110 is substantially straight between the output region of the fluid channel inlet 120' and the fluid channel outlet 140, but rotated by 90° at the junction 125', in order to provide a more compact and non-interfering interface with the sample sectioning module 103.

In the specific example of the fluid channel 110', the fluid channel 110 includes a chute 135' fluidly coupled between the fluid channel inlet 120' and the section-mounting region 130', wherein the chute 135' is configured to slope in a declined manner from the elevated lip 127' of the fluid channel inlet 120; toward the section-mounting region 130'. As such, the chute 135' provides downhill flow for acceleration of the section with fluid in the fluid channel 110'. The slope of the declined portion is defined in FIG. 2 as β and is defined as being from 5-15° in the specific example, and the section-mounting region 130' is substantially flat relative to a horizontal plane, such that the slope β of the fluid channel 110 transitions from being declined upstream of the section-mounting region 130' to being flat, relative to a horizontal plane, at the section-mounting region 130'.

Figure 10:
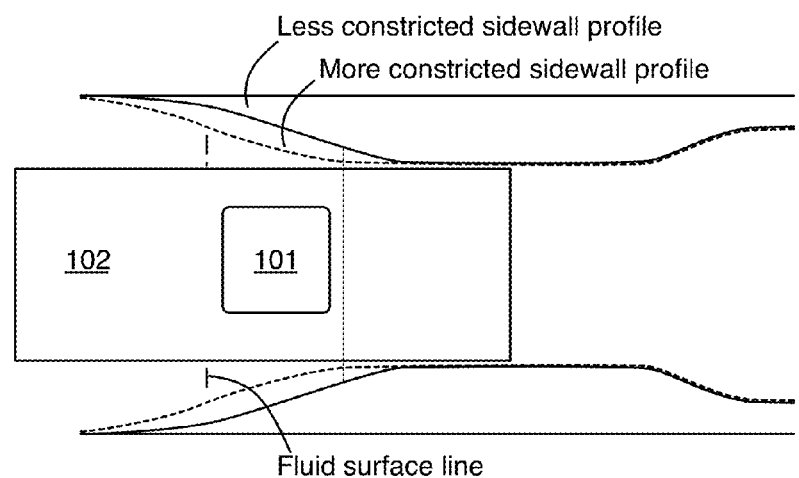
FIG. 10 depicts variations of sidewall configurations in an embodiment of a system for mounting a section to a substrate.

In the specific example of the fluid channel 110, the channel width is initially substantially wider than (e.g., 115-300%) the width of a section 101 generated at the sample sectioning module 103, but this width is then reduced, proximal to the section-mounting region 130', to a width that is marginally wider (e.g., 105-125%) than the width of the section 101 by sidewall contours of the fluid channel, in order to enable more accurate positioning of the section within the section-mounting region 130. In the specific example of the fluid channel, the section-mounting region 130 comprises a receiving area including a contoured surface 133 at a base surface of the receiving area that is configured provide a biasing force that aligns the section toward a desired position at a substrate 102 within the section-mounting region 130. Variations of the specific example of the fluid channel 110 can, however, be configured in any other suitable manner and comprise any other suitable fluidic elements that enable accurate and repeatable positioning of sections at one or more substrates within the section-mounting region 130. Adjustable sidewall profiles, for instance, and as shown in FIG. 10, can be used to alter an amount of flow restriction about a substrate 102 to control fluid level heights, control fluid level modulation rates, accommodate samples of varying size, and/or adjust lateral positioning of a section 101 at a substrate 102.

1.2 System—Reservoir, Manifold, and Filter

As noted above, the reservoir 150 is in fluid communication with the fluid channel outlet 140, and functions to provide a bath of fluid that can be delivered into the fluid channel 110 by way of the fluid channel inlet 120. The reservoir is preferably configured to receive fluid (e.g., filtered fluid) from the fluid channel outlet 140 for recirculation into the system, in order to enable reuse of a substantially fixed volume of fluid flowing throughout the system 100. As such, the system 100 preferably includes a single reservoir that allows for fluid recirculation, wherein the single reservoir can be refilled, if needed (e.g., due to fluid loss in evaporation, etc.). However, variations of the system 100 can alternatively include any suitable number of reservoirs (e.g., a reservoir for fluid delivery into the fluid channel inlet 120 and a waste reservoir configured to receive waste fluid from the fluid channel outlet 140) that enable fluid flow into the fluid channel inlet 120 and fluid flow out of the fluid channel outlet 140.

The reservoir 150 preferably contains a volume of fluid that has desired properties in facilitating transmission of a section 101 along the fluid channel 110, and mounting of the section 101 onto a substrate 102 at the section-mounting region 130. In variations, the fluid can be characterized as one or more of: low-viscosity (e.g., less than $1 \times 10^{-3}$ Pa*s), volatile at temperatures for histological section processing (e.g., volatile at room temperature, volatile within a sample drying environment), non-interacting with histological process reagents (e.g., histological stains, etc.) to prevent generation of specimen artifacts, non-damaging to a biological specimen of a sample, neutral pH, and inexpensive. Preferably, the fluid circulating through the system 100, by way of the reservoir 150, comprises water; however, alternative variations of the fluid can comprise any other suitable fluid for histological section processing. In some variations, an additive can be introduced and/or neutralized to modify surface tension of the fluid to promote better transport of a section 101 through the fluidic channel, and/or to promote enhanced interactions with a substrate 102. In one such example, a hydrophilic additive can be introduced with fluid from the reservoir to promote improved transport of a section 101 through the fluidic channel 110.

The manifold 160 is fluidly coupled to the reservoir 150, and functions to delivers fluid from the reservoir 150 to the fluid channel inlet 120, thereby transmitting fluid flow that drives delivery of the section from the fluid channel inlet 110 toward the section-mounting region 130. The manifold is configured to provide a flow path between the reservoir 150 and the fluid channel inlet 120, thereby enabling separation of a section 101 from an adjoining section produced by the sample sectioning module 103, facilitating delivery of the section 101 from the fluid channel inlet 120, and transmitting the section toward the section-mounting region 130 of the fluid channel 110. Preferably, fluid from the reservoir 150 is pumped through one or more tubes 159 into the manifold 160, as shown in FIG. 6A, wherein the manifold 160 is configured to divide the flow into a set of openings 162 into the fluid channel inlet 120. As such, the manifold 160 is preferably configured to generate laminar flow at the fluid channel inlet 120; however, the manifold 160 can alternatively be configured to generate any other suitable type of flow (e.g., turbulent flow) at the fluid channel inlet 120.

Figure 11:
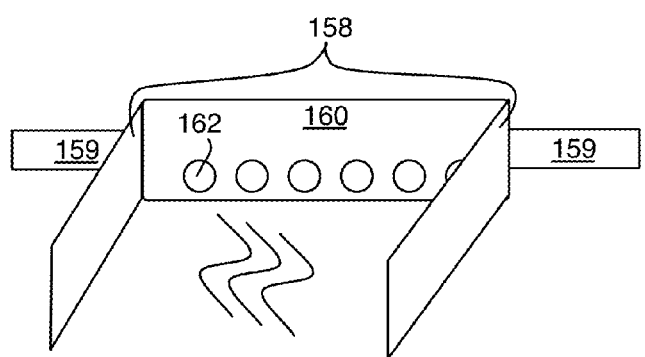
FIG. 11 depicts a variation of a manifold in an embodiment of a system for mounting a section to a substrate.
Figure 12:
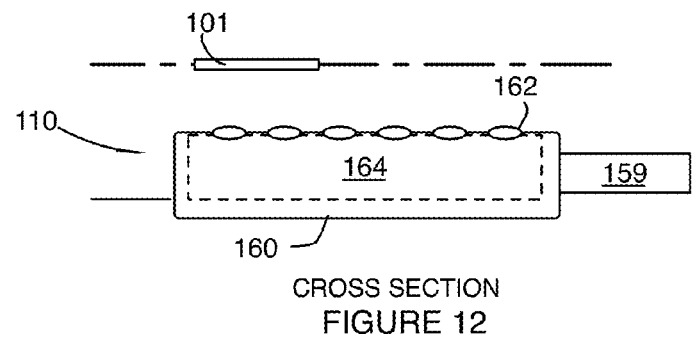
FIG. 12 depicts a variation of a manifold in an embodiment of a system for mounting a section to a substrate.

In one variation, as shown in FIG. 11, the manifold 160 has at least two inlet tubes 159 into the manifold 160 that provide a uniform (e.g., symmetric) distribution of flow across the openings 162 of the manifold 160 with negligible flow resistance. In this variation, the inlet tubes 159 are oriented in an opposing manner at opposite sides 158 of the manifold, wherein the opposite sides 158 are substantially parallel with sidewalls defining a longitudinal axis of fluid flow through the fluid channel 110. In this variation, the set of openings 162 can be arranged in one or more of: a linear manner that defines a plane of fluid flow substantially parallel to that of a base surface of the fluid channel 110; a linear manner that defines a plane of fluid flow substantially non-parallel to that of a base surface of the fluid channel 110; a non-linear manner (e.g., curved manner defining a concave surface of fluid flow, curved manner defining a convex surface of fluid flow, staggered manner, etc.); and in any other suitable manner. In another variation, the manifold 160 can have an elongated opening 163 and/or an orifice pattern with a suitably apodized density, which can function to provide laminar flow into the fluid channel inlet 120 and distribute it more evenly across the opening(s) 162, thereby eliminating the need for a second inlet tube 159 into the manifold. In another variation, the openings of the set of openings can be integrated into a single tube at varying angles in order to facilitate manipulation (e.g., separation) of the tissue sections. In yet another variation, as shown in FIG. 12, the manifold 160 can comprise a cavity 164 inferior to a surface with openings 162, wherein fluid from the reservoir 150 is delivered into the cavity 164, thereby allowing distribution of the set of openings 162 of the manifold across a surface (e.g., a planar surface parallel to a base surface of the fluid channel 110) in a 2D or 3D configuration, rather than in a linear configuration. In yet another variation, the manifold 160 can be configured to deliver fluid from the reservoir 150 to one or both of the sidewalls of the fluid channel 100, to produce flow in a direction non-parallel to a longitudinal axis of the fluid channel 110. However, the manifold 160 can be configured to deliver fluid from the reservoir 150 and into the fluid channel inlet 120 using any other suitable 1D, 2D, or 3D configuration of openings 162, or in any other suitable manner.

The manifold 160 is preferably in fluid communication with a pump 167 coupled between the reservoir 150 and the manifold, as shown in FIG. 1, wherein modulation of behavior of the pump 167 is governed by a controller 168. The pump 167 can be configured to provide positive pressure and/or negative pressure in driving fluid between the reservoir 150 and the manifold 160. As such, in one mode, forward flow generated by the pump 167 can facilitate forward movement of a section 101 through any portion of the fluid channel 110, and in another mode, reverse flow generated by the pump 167 can facilitate reverse movement of a section 101 through any portion of the fluid channel 110. Furthermore, forward and/or reverse flow can be adjustable to provide desired flow parameters (e.g., velocities, etc.) for processing of a single section or multiple sections in sequence. Modulation of flow (e.g., with a brief period of elevated flow rate) can additionally or alternatively be used to provide a biasing force that delivers a section 101 toward a substrate 102 for mounting.

In one variation, the pump 167 is a positive displacement pump, and in an example of this variation, the pump 167 is a peristaltic pump. In other examples, the pump 167 can include any one or more of: a gear pump, a screw pump, a piston pump, a progressing cavity pump, a roots-type pump, a plunger pump, a diaphragm pump, a rope pump, an impeller pump, and any other suitable type of pump. Furthermore, the system 100 can include more than one pump 167 configured at desired positions relative to the fluidic channel 110, the reservoir 150, and the manifold 160. The pump 167 preferably has a known flow rate to pump speed ratio, such that control of the speed of the pump 167 corresponds to a control of the flow rate of the fluid within the fluid channel 110. Furthermore, the pump 167 is preferably configured within the system 100 such that the system 100 is relatively easy to assemble, light to haul, quick to control, and easy to clean.

The controller 168 is preferably configured to respond to inputs provided by an operator of the system 100, in modulating flow parameters of fluid within the system 100. In one variation, the controller 168 can be configured to access a lookup table that facilitates correlation of an input from an operator of the system 100 to a desired flow parameter (e.g., flow rate) of the fluid within the fluid channel 110. The lookup table preferably includes data based on one or more of: historical behavior of the system 100, historical runs of other units of the system 100, empirical data conducted and developed by the manufacturer or developer of the system 100, and any other suitable data. The stored information preferably includes the type of fluid circulating throughout the system, characteristics (e.g., dimensions, embedding medium, etc.) of sections generated by a sample-sectioning module 103 in communication with the system 100, number of sections being processed by the system 100 at a given time, potential errors in performance by the system 100, and any other suitable information. The controller 30 can also be further adapted to access the lookup table via a computer processing network.

In another variation, the controller 168 can include a storage device with accessible memory. A user interface at which an operator provides inputs for control of the system 100, along with the accessible memory of the storage device, can thus permit the operator to access stored information about runs of the system 100 and the system configuration and settings that were utilized during those runs. The stored information can include one or more of: the type of fluid circulating throughout the system, characteristics (e.g., dimensions, embedding medium, etc.) of sections generated by a sample-sectioning module 103 in communication with the system 100, number of sections being processed by the system 100 at a given time, a history of errors in performance by the system 100, and any other suitable information. This stored information can be accessed by the operator and retrieved by the controller 168 and/or systems. The operator can then, by interfacing with the controller 168, automatically set up the flow parameters for the system 100, by utilizing those previous sample run settings. Furthermore, once a run of the system 100 has been completed, an operator can save the controller settings and use the saved information for future runs for processing similar sections or specimens.

Flow modulation within the system 100 can, however, be additionally or alternatively enabled by using one or more valves that adjust flow (e.g., redirect flow, stop flow, open flow, etc.) to different reservoirs (e.g., a buffer reservoir) within or relative to the fluid channel 100. Additionally or alternatively, a gate can be used to temporarily block passage of flow upstream of the section-mounting region 130, thereby creating a desired drop in fluid level at the section-mounting region 130, independent of a speed of operation of the pump 167. The gate can also function to prevent a section from drifting back in an upstream direction. In operation, if pump speed remains unaltered, a fluid level on an upstream side of the gate will temporarily rise until the gate is removed from an obstructing position. Automation of action of the valve(s) and/or gate(s) can be facilitated by the controller 168 described above, or any other suitable element.

As noted above, in some embodiments, the system 100 can additionally or alternatively include a filter 170, fluidly configured between the fluid channel outlet 140 and the manifold 160, as shown in FIG. 1, that functions to prevent undesired substances from flowing into the fluid channel inlet 120. The filter 170 preferably has a physical membrane that prevents substances having a governing dimension above a threshold size (e.g., defined by pores in the membrane); however, any other suitable mechanism can facilitate filtration of undesired substances from the fluid channel 110. In one variation, the filter 170 can be configured immediately downstream of the fluid channel outlet 140, in order to prevent undesired substances from entering the reservoir 150. Additionally or alternatively, the system 100 can include a filter 170 configured within the reservoir, but upstream of the pump 167, in order to prevent undesired substances from affecting proper function of the pump 167 and/or reaching the manifold 160 during recirculation of fluid into the fluid channel 110. Additionally or alternatively, the filter 170 can be configured at any other suitable portion of a fluid loop defined across the manifold 160, the fluid channel 110, and the reservoir 150. The filter 170 is preferably configured to be a replaceable element of the system 110 in order to promote ease of maintenance; however, the filter 170 can alternatively be configured in any other suitable manner. Variations of the system 100 can include a single filter, or can alternatively include multiple filters configured to provide redundancy in removing undesired substances from the fluid loop of the system 100.

1.3 System—Substrate Actuation Module

The system 100 can additionally or alternatively include a substrate actuation module 190 that transmits the substrate into the section-mounting region in a first operation, and delivers the substrate from the section-mounting region, with the section mounted to the substrate, in a second operation. The substrate actuation module 190 is configured to couple to an imaging substrate 102, and functions to move the substrate relative to the section-mounting region 130 of the fluid channel 110 to facilitate placement of a section 101 onto the substrate 102 in an accurate and repeatable manner.

As shown in FIG. 6A, the substrate actuation module 190 can comprise a gripper 191 configured to couple to at least one surface 106 of a substrate 102 (e.g., glass slide), without obstructing mounting of a section 101 to the substrate, by any one or more of: friction, adhesion, compressive force, and any other suitable mechanism, in a manner that is consistent across all imaging substrates utilized by the system 100. Furthermore, the substrate actuation module 190 preferably comprises an actuator 192 configured to induce motion of the gripper 191 and/or the imaging substrate along a path relative to a section at the section-mounting region 130 of the fluid channel. In one variation, the actuator 192 is a linear actuator configured to transmit the imaging substrate along a linear and sloping path into a reservoir of fluid defined at the section-mounting region 130 (e.g., immediately downstream of a section at the section-mounting region 130), as described above; however, the actuator 192 can alternatively be configured to transmit the substrate 102 along any other suitable path that facilitates mounting of the section 101 onto the substrate 102. The path along with the actuator 192 transmits the substrate 102 can be constrained by a rail 193, as shown in FIG. 6A or can alternatively be constrained or unconstrained in any other suitable manner.

Preferably, actuation in the substrate actuation module 190 is configured to coordinate with flow, from the fluid channel inlet 120, to the section-mounting region 130 and out of the fluid channel outlet 140. As such, the substrate actuation module 190 is preferably configured to cooperate with or be co-governed by the controller 168 of the pump 167, in synchronizing flow of fluid through the system 100 and mounting of sections 101 to substrates 102 by way of the substrate actuation module 190. In some variations, a flow rate into the fluid channel 110 can be reduced or halted by the controller 168 of the pump 167 to stabilize a position of the section 101 at the section-mounting region 130 prior to mounting; however, flow can be adjusted in any other suitable manner and with any suitable sequence that facilitates mounting of the section 101 to a substrate 102.

Figure 13A:
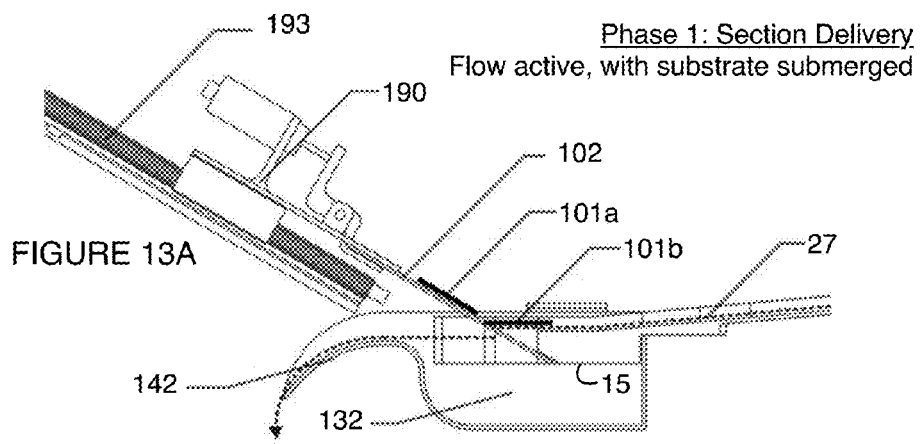
FIGS. 13A-13C depict phases of an example workflow implemented by an embodiment of a system for mounting a section to a substrate.
Figure 13B:
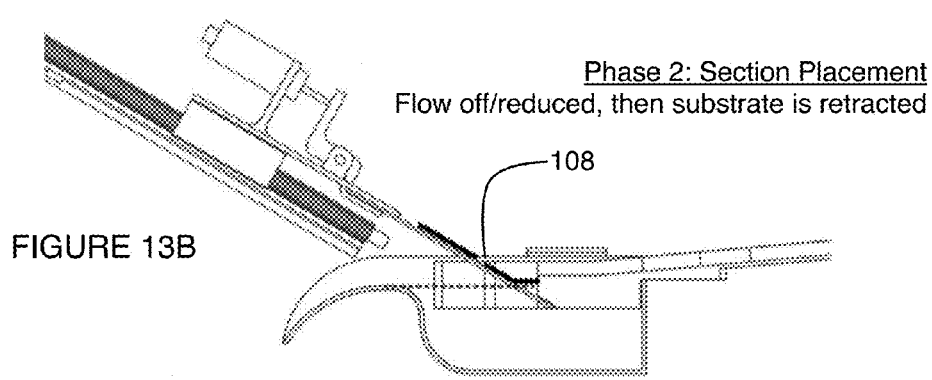
Figure 13C:
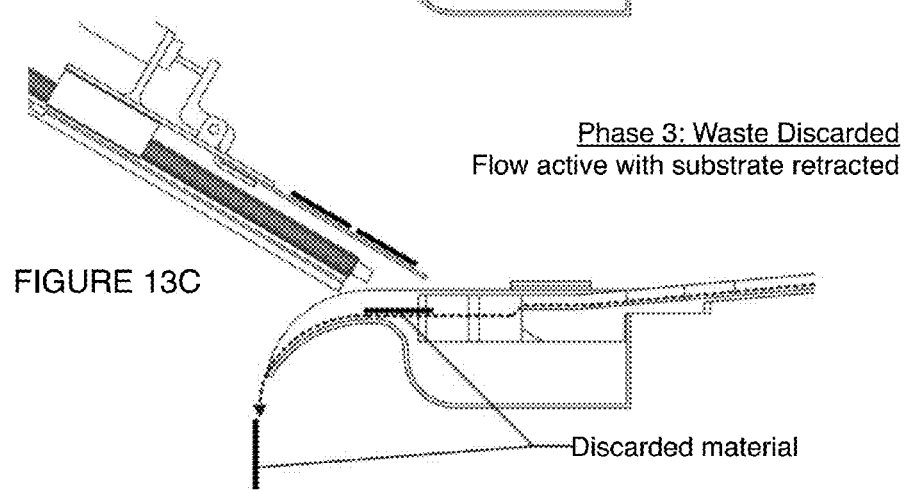
Figure 14:
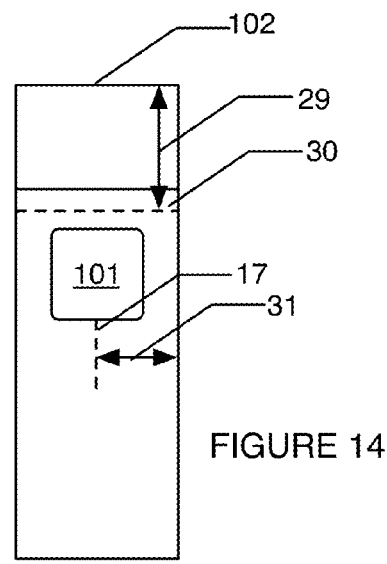
FIG. 14 depicts example portions of a substrate and section in an embodiment of a system for mounting a section to a substrate.

In an example operation of the substrate actuation module 190, as shown in FIGS. 13A-13C, the substrate actuation module 190 coordinates with flow into the fluid channel 110 as governed by the controller 168 of the pump 167. In a first phase of the example operation, as shown in FIG. 13A, a section 101b has been transported to the section-mounting region 130, as driven by fluid flow into the fluid channel 110 by the pump 167. In the first phase of the example operation, flow is provided into the fluid channel 110 to bring the section 101 toward the section-mounting region 130, with a substrate 102 partially submerged within the section-mounting region 130 by the substrate actuation module 190. In the phase portion of the example operation, as shown in FIG. 13A, a section 101a has already been mounted to the substrate 102, and an additional section 101b is in position, at the section-mounting region 130, to be mounted to the substrate 102. In the state shown in FIG. 13A with regions of the substrate 102 and section 101 defined in FIG. 14, the fluid level 27 in the fluid channel 110 is lower downstream of the substrate 102 than it is upstream of the substrate 102, and the base surface 15 and sidewall 14 geometries of the fluid channel 110 at the section-mounting region 130 are configured to constrain the section 101b to a desired lateral substrate position 31. The sidewalls 14 of the fluid channel 110, as shown in FIG. 6A, then widen around the substrate 102 at the section-mounting region 130 to provide a surface water velocity sufficient to maintain a position of the section 102b intended to be mounted, even during flow speed reduction induced by the controller 168. In the example operation, the sidewalls 14 are sufficiently close to the substrate 105 sides to provide enough construction, such that a drop in the fluid level 27 across the substrate 102 occurs during mounting of the section 101b to the substrate 102. In the first phase of the example operation, shown in FIGS. 13A and 14, the depth that the substrate 102 is submerged in the section-mounting region 130 establishes a line of juncture 30 between fluid in the section-mounting region 130 and the top of the substrate 102, and therefore a vertical position 29 of the section 101b being mounted to the substrate 102.

In a second phase of the example operation, as shown in FIG. 13B, reducing the flow rate of fluid in the fluid channel 110 causes the section 101b to be secured to the substrate 102. An edge 108 of the section 101b that is in contact with the substrate 102 is the first portion of the section 101b to be mounted to the slide, and as the fluid level equilibrates within the section-mounting region 130, more of the section 101b is mounted to the substrate 102. In the second portion of the example operation, the entire section 101b is mounted onto the substrate 102 prior to mechanical retraction of the substrate from the section-mounting region 130 by the substrate actuation module 190; however, variations of the example operation can include any other suitable workflow that does not involve mounting of an entire section 101b prior to retraction of the substrate 102 from the section-mounting region 130. For instance, only a portion of the section 101b can be laid onto a substrate 102 by flow modulation in the fluid channel 110, and mechanical retraction of the substrate 102 from the section-mounting region 130 by the substrate actuation module 190 consummates mounting of the section 101b to the substrate by way of substrate withdrawal and an adhesion force produced by fluid between the section 101b and the substrate 102. Alternatively, mechanical retraction of the substrate 102 from the section-mounting region 130 can cause application of the section 101b to the substrate 102 substantially without modulation of a flow rate within the fluid channel 110 by the controller 168 of the pump 167. Additionally or alternatively, modulation (e.g., lessening) of an angle of a substrate 102 within the section-mounting region 130, by the substrate actuation module 190, can be used to apply a section 101b onto a substrate.

In a third portion of the example operation, as shown in FIG. 13C, retraction of the substrate 102 from the section-mounting region 130 provides a flow path (e.g., an unobstructed path) that allows undesired substances 28 (e.g., debris and discarded sections) to be removed by flowing out of the fluid channel outlet 140, and optionally, through a filter 170.

1.4 System—Temperature Regulation and Wrinkle Removal Module

As shown in FIG. 1, the system 100 can additionally or alternatively include a temperature regulating module 180 in contact with fluid from the reservoir, that adjusts a temperature of fluid within the fluid channel. As such, in facilitating mounting of sections at substrates, fluid from the reservoir 150 or portions of the fluid channel 110 can be transmitted at a desired temperature throughout the system. The desired temperature is preferably contained within a range of temperatures having a higher limiting temperature and a lower limiting temperature. The higher limiting temperature is preferably configured such that an embedding medium (e.g., paraffin wax) surrounding a specimen of a section 101 does not completely melt, and the lower limiting temperature is preferably configured such that the section 101 does not contract in a manner that could cause wrinkling or other damage of the section 101.

In one variation, the temperature-regulating module 180 can be in communication with reservoir 150 in a manner that provides regulation of the temperature of fluid within the reservoir 150, as it is transmitted from the reservoir 150 into the fluid channel inlet 120. As such, temperature of the fluid at the reservoir 150 can be adjusted prior to delivery into the fluid channel 110. Additionally or alternatively, the temperature-regulating module 180 can be in communication with any arbitrary position in the flow path of the fluid channel 110 to create a localized temperature profile at a desired portion of the fluid channel 110, without requiring regulation of the entire volume of fluid in the reservoir 150. In yet another alternative variation, the temperature-regulating element may induce indirect (e.g., non-contact) temperature variation of a section 101 at any point along flow through the fluid channel 4 (e.g., by air convection or radiant/infrared heating) without requiring direct thermal conduction between fluid in the fluid channel 110 or fluid at the reservoir 150, and a temperature-regulating module 180. The reservoir 150 and/or the fluid channel 110 can, however, be configured in any other suitable manner.

Figure 15:
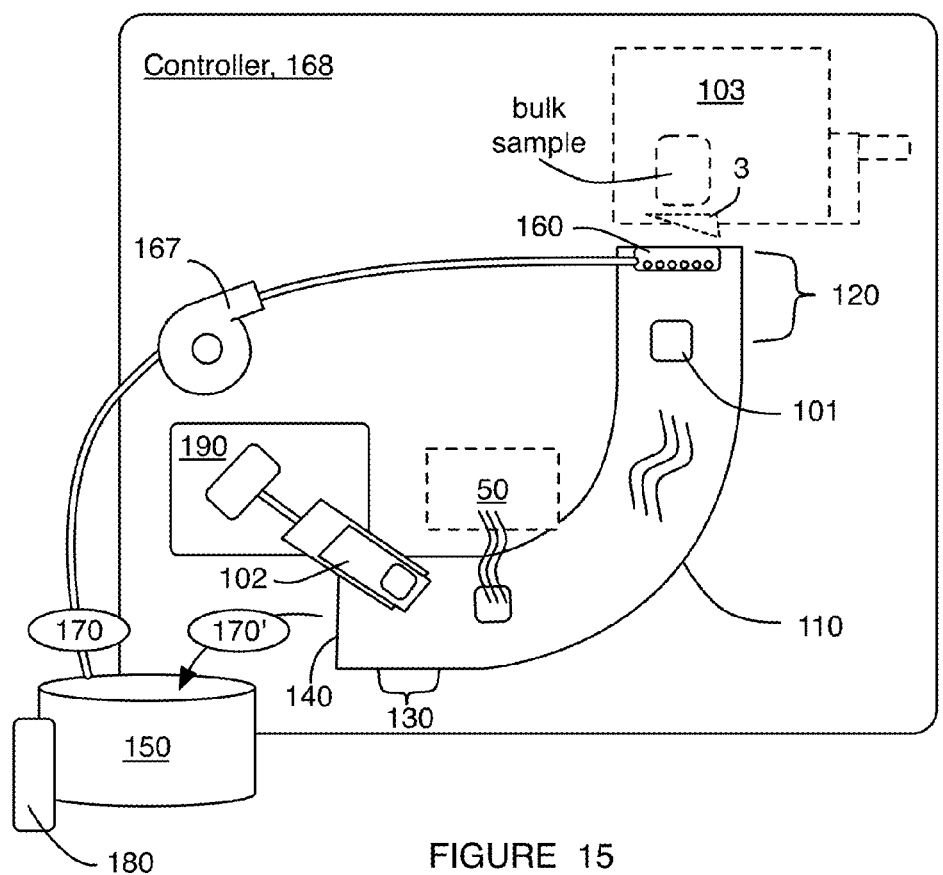
FIG. 15 depicts a schematic of an embodiment of a system for mounting a section to a substrate.
Figure 16:
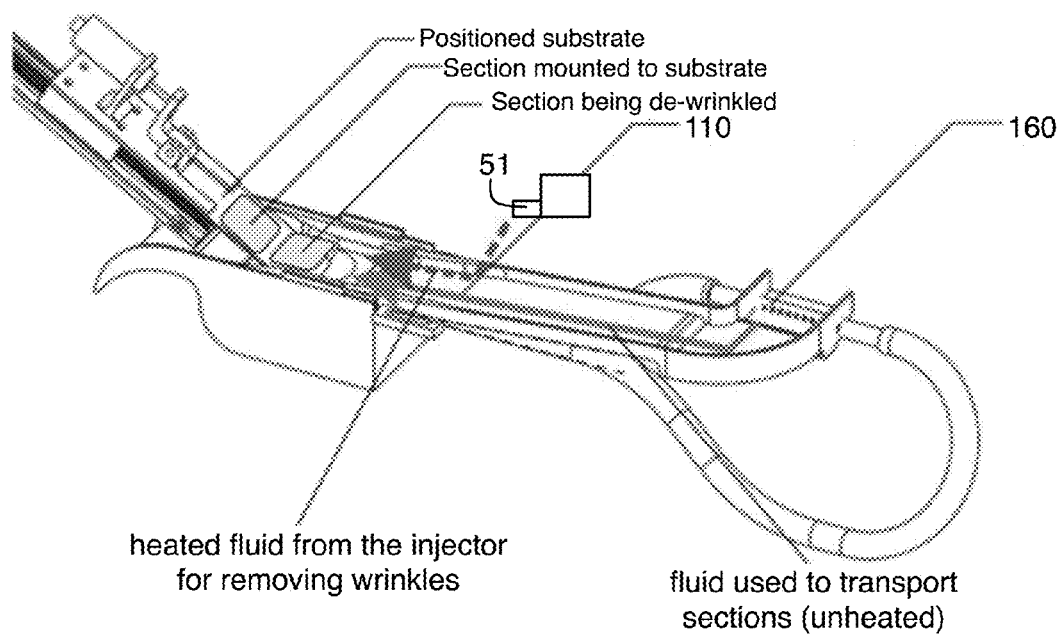
FIG. 16 depicts a portion of an embodiment of a system for mounting a section to a substrate.

The system 100 can additionally or alternatively include a wrinkle-removal module 50, as shown in FIGS. 6 and 15, that functions to reduce or eliminate any wrinkling of sections prior to or during mounting to a substrate 102. The wrinkle-removal module 50 can be configured proximal to the section-mounting region 130 of the fluid channel 110, and functions to affect a local fluid parameter near a section in the section-mounting region 130, such that the section 101 is substantially void of wrinkles prior to, during, and/or after coupling of the section 101 to a substrate 102. The wrinkle-removal module 50 preferably modulates a local fluid temperature within the section-mounting region 130, in coordination with delivery of the section 101 from the fluid channel inlet 120 to the section-mounting region 130, as facilitated by the controller 168 of the pump 167. As such, in a first variation, an example of which is shown in FIG. 16, the wrinkle-removal module 50 can include an injector 51 configured to inject a volume of fluid (e.g., from the reservoir, from another fluid source) into the fluid channel 110 proximal the section-mounting region 130, wherein fluid from the injector 51 is at a temperature configured to increase fluidity of the section (e.g., a wax section) within the section-mounting region 130. In this variation, the temperature of the fluid from the injector 51 is preferably elevated relative to a global fluid temperature within the fluid channel, to provide a local fluid temperature (e.g., to 40-60° C.) that increases fluidity of the section without complete dissociation or melting of the section. However, fluid can alternatively be provided from the injector 51 at any other suitable temperature that facilitates wrinkle removal in a section. In this variation, the system 100 can include a switch (e.g., 3-way switch) configured to switch between a first configuration in which fluid at a lower temperature from the reservoir 150 is circulated into the fluid channel 110 by way of the fluid channel inlet 120, and a second configuration in which fluid at an elevated temperature (e.g., as passed through a heating apparatus upstream of the injector 51) is circulated into the fluid channel 110 by way of the injector 51. Additionally or alternatively, a flow rate used to deliver fluid at an elevated temperature from the injector 51 can be higher, lower, or substantially equal to a flow rate used to deliver fluid at a lower temperature into the fluid channel inlet 120.

Figure 17A:
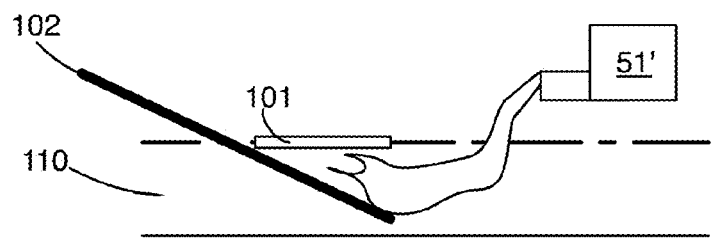
FIGS. 17A-17C depict configurations of variations of an injector in an embodiment of a system for mounting a section to a substrate.
Figure 17B:
Figure 17C:
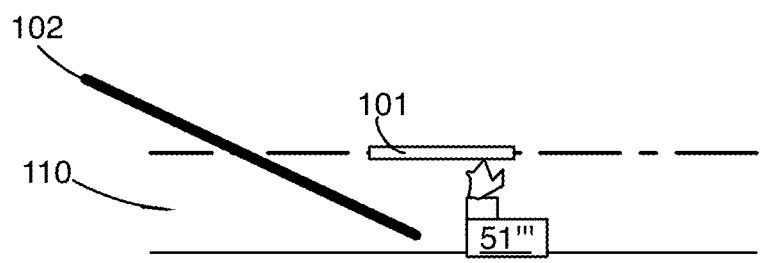

In a first example of the first variation, the injector 51' can be positioned superior to and upstream of the section-mounting region 130, as shown in FIG. 17A, in order to inject high-temperature fluid into the fluid channel 110 upstream of the section-mounting region 110, such that the high-temperature fluid flows under a section within the section mounting region 130 to remove any wrinkles in the section, prior to mounting of the section 101 to a substrate 102. In a second example of the first variation, as shown in FIG. 17B, the injector 51" can be positioned downstream of the section-mounting region 130 and configured to inject high-temperature fluid upstream into the section-mounting region 130, in order to remove any wrinkles in a section within the section-mounting region 130. In a third example of the first variation, as shown in FIG. 17C, the injector 51''' can be positioned directly inferior to a section 101 within the section-mounting region 130 (e.g., at a base surface of the fluid channel 110, within a reservoir into which the imaging substrate is directed for mounting of the section), such that high-temperature fluid is injected in an inferior-to-superior direction, toward the section 101, to remove any wrinkles. In one variation of the third example, the fluid channel 110 can include a reservoir proximal the section-mounting region 130, at which the section is held stationary and exposed to fluid at an elevated temperature, from the injector 51, prior to mounting of the section to the imaging substrate. In another variation of the third example, a substrate 102 can be positioned (e.g., at an angle, perpendicularly) with an edge against the base surface of the fluid channel 110 proximal the section-mounting region 130 to create a dam, fluid at an elevated temperature can be delivered toward the imaging substrate from the injector 51 and trapped by the dam formed by the imaging substrate, and a section 101 positioned upstream of the dam can thus be positioned over a volume of fluid at an elevated temperature to undergo de-wrinkling. Then, the substrate can be positioned away from the base surface of the fluid channel 4, thereby breaking the dam and allowing the section to be mounted to the imaging substrate, free of wrinkles, as the fluid level in the fluid channel 110 drops.

In a fourth example of the first variation, the injector 51 can be configured to deliver high-temperature fluid from sidewalls of the fluid channel 110 proximal section-mounting region 130, in order to remove any wrinkles in a section within the section-mounting region. In a fifth example of the first variation, the injector 51 can be configured to deliver fluid at an elevated temperature through the same manifold 160 used to deliver fluid from the reservoir 150 into the fluid channel inlet 150, in order to provide fluid at a suitable temperature for de-wrinkling of a section. In one variation of the fifth example, the entire volume of fluid from the reservoir 150 can be elevated to a desired temperature for de-wrinkling of a section, and delivered through the manifold 160, by the injector, such that all fluid flowing within the fluid channel 110 is elevated to the desired temperature. In any of the above examples of the first variation, the section 101 can be held stationary by the substrate 102 or any other suitable object as fluid from the injector 51 flows under the section. Furthermore, a length of time over which the section 101 sits atop fluid at an elevated temperature can be adjusted according to requirements of a sample-type (e.g., tissue type) of the section, for instance, by adjusting flow rates of fluid into the fluid channel 110 and/or adjusting a position of the section by way of the substrate actuation module 190. Variations of the injector 51 of the first variation can, however, be configured in any other suitable manner or implement combinations of any of the above examples/variations.

Figure 18:
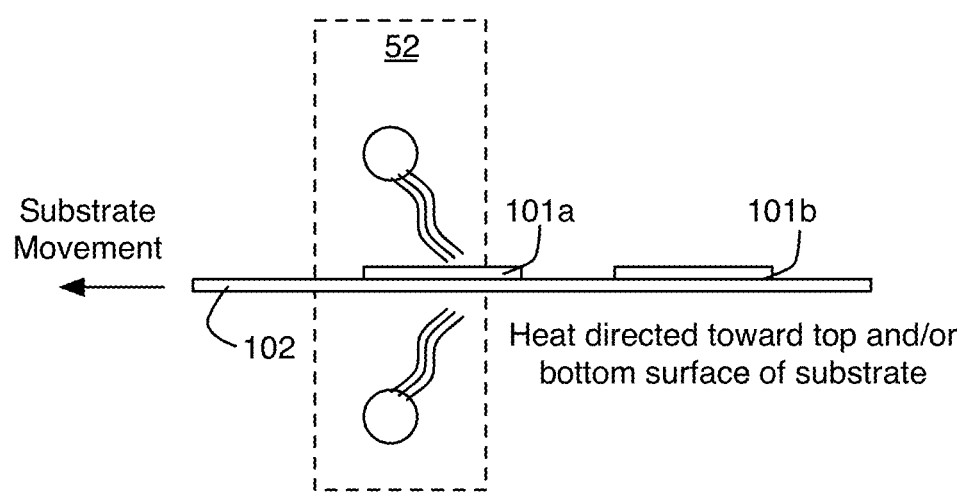
FIG. 18 depicts an additional variation of a wrinkle removal module in an embodiment of a system for mounting a section to a substrate.

In a second variation of the wrinkle-removal module 50 involving local temperature adjustment, the wrinkle-removal module 50 can additionally or alternatively include a heating module 52 configured to provide convective and/or radiant heat transfer toward a section at the section-mounting region 130. As shown in FIG. 18, the heating module 52 can be configured to transmit heat toward one or more surfaces of the section 101, from a direction superior to and/or inferior to the section 101. Furthermore, the heating module 52 can be configured to deliver heat toward the section prior to, during, and/or after contact between the section and a surface of a substrate 102. As such, the heating module 52 can be configured to transmit heat toward the section 101 by locally heating fluid within the section-mounting region 130 and/or by transmitting heat through air toward a surface of the section 101 at the section-mounting region 130, with or without a substrate 102 present. In a first example of the second variation, the heating module 52 can comprise a heating element positioned at a base surface of the section-mounting region 130 and inferior to a section at the section-mounting region 130, such that the heating element locally heats fluid (e.g., by convective heat transfer) at an inferior surface of the section, thereby facilitating wrinkle removal. In a second example of the second variation, the heating module 52 can comprise heating elements spanning sidewalls of the fluid channel 110 proximal to (e.g., upstream of, adjacent to, downstream of, etc.) the section-mounting region 130, such that the heating elements locally heat fluid (e.g., by convective heat transfer) from lateral directions to facilitate wrinkle removal. In a third example of the second variation, the heating module 52 can comprise a heating element positioned superior to a section at the section-mounting region 130, configured to provide radiant and/or convective heat transfer through air toward the section at the section-mounting region 130. In one variation of the third example, heated air from the heating module 52 can be delivered toward a substrate 102 with the section 101, in order to heat the section 101 and residual fluid between the section and the imaging substrate to provide a de-wrinkling mechanism. Variations of the heating module 52 of the second variation can, however, be configured in any other suitable manner or implement combinations of any of the above examples/variations. Furthermore, delivery of heat from the heating module 52 to the section can be performed multiple directions simultaneously, and/or in any other suitable sequence of directions.

Figure 19:
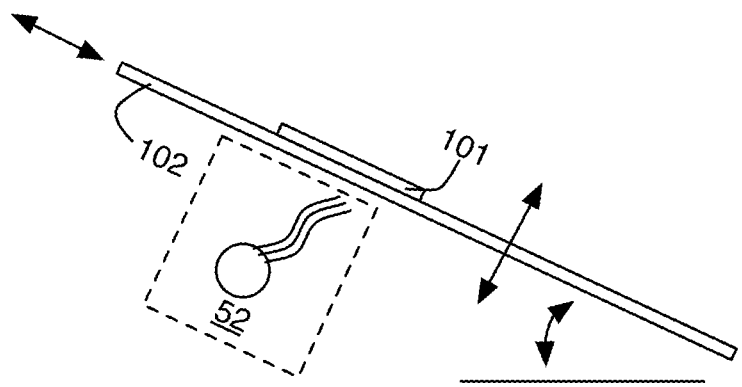
FIG. 19 depicts different configurations of a wrinkle removal module and substrate in an embodiment of a system for mounting a section to a substrate.

In any of the above examples and variations, the injector 51/heating module 52 can be configured cyclically or non-cyclically vary temperatures proximal to a section within the section-mounting region 130, in order to induce thermal expansion and contraction of the section 101. In these variations, repeated expansion and/or contraction of the section can allow removal of any wrinkles that would remain after a single instance of heating of the section. Furthermore, in any of the above examples and variations, the injector 51/heating module 52 can be configured to move (e.g., by coupling to an actuator) relative to a section 101 (e.g., by moving the injector/heating module, by moving an imaging substrate or the section relative to the injector/heating module) at the section-mounting region 130, such that heat can be provided consistently to sections at the section-mounting region 130 in a dynamic manner. Moving and/or adjusting an angle of a substrate 102 with the section 101 relative to a heating module 52 can, for instance, facilitate wicking of fluid from the substrate 102 and facilitate drying of a section 101 during de-wrinkling, as shown in FIG. 19. Heating by the wrinkle-removal module 50 can furthermore be performed continuously as a stream of sections flow into the section-mounting region, or intermittently, for each section that flows in the section-mounting region.

Figure 20:
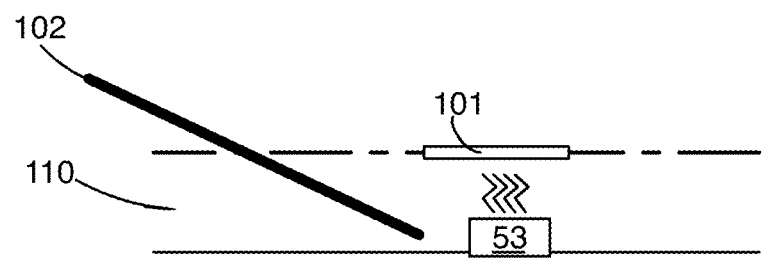
FIG. 20 depicts an additional variation of a wrinkle removal module in an embodiment of a system for mounting a section to a substrate.

In alternative variations, the wrinkle-removal module 50 can adjust local fluid behavior (e.g., flow behavior, viscosity behavior, etc.) proximal to a section within the section-mounting region 130, in order to facilitate wrinkle removal within a section for mounting. In one alternative variation, the wrinkle-removal module 50 can generate uniformly or non-uniformly diverting flows proximal to (e.g., directly inferior to) a section at the section-mounting region 130 that provide forces that expand the section. In examples of this variation, the diverting flows can include two or more flow paths directed outward from a point proximal to a center point of a section 101 at the section-mounting region 130. In another alternative variation, the wrinkle-removal module 50 can include an injector configured to transmit a fluid, different from fluid flowing from the fluid channel inlet 120 to the fluid channel outlet 140, that provides an expanding force (e.g., based upon differences in density, based upon differences in viscosity, etc.) at a surface of a section 101 at the section-mounting region 130. In another alternative variation, as shown in FIG. 20, the wrinkle-removal module 50 can include a vibration module 53 configured to generate vibration waves proximal to a section at the section-mounting region 130, in order to facilitate wrinkle removal. In examples of this variation, the vibration module 53 can be configured to generate vibrations mechanically and/or acoustically, and can be configured to generate standing and/or non-standing waves. Variations of the wrinkle-removal module 50 can, however, comprise any other suitable elements configured to facilitate wrinkle removal by any other suitable mechanism.

Figure 21:
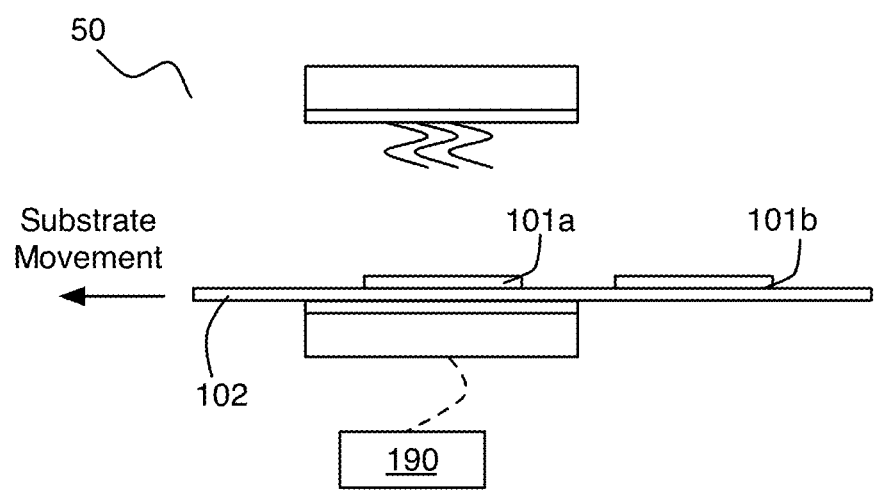
FIG. 21 depicts an additional variation of a wrinkle removal module in an embodiment of a system for mounting a section to a substrate.

In still alternative variations, the wrinkle removal module 50 can be configured to transfer heat to the substrate 102, in order to increase the temperature of the substrate 102 to remove wrinkles in a section 101 that contacts the heated substrate 102. As such, the wrinkle removal module 50 can comprise a heating element (e.g., heating plate, array of heating chips, etc.) configured to contact at least one surface of the substrate 102 and/or radiate heat toward the substrate 102, as shown in FIG. 21, prior to or during mounting of the section 101 to the substrate 102 in order to remove wrinkles in the section 101. In specific examples, the heating element can be integrated with the substrate actuation module 190 that is configured to manipulate motion of the substrate 102, or can be configured to contact the substrate 102 in any other suitable manner.

Furthermore, the wrinkle-removal module 50 can be configured to coordinate with flow, from the fluid channel inlet 120, to the section-mounting region 130, as facilitated by the controller 168 of the pump 167 coupled to the manifold 160. In some variations, a flow rate into the fluid channel 110 can be reduced or halted to stabilize a position of the section at the section-mounting region 130, thereby facilitating wrinkle removal within the section 101. Flow within the fluid channel 110 can, however, be configured in any other suitable manner in coordination with the wrinkle-removal module 50.

Figure 22A:
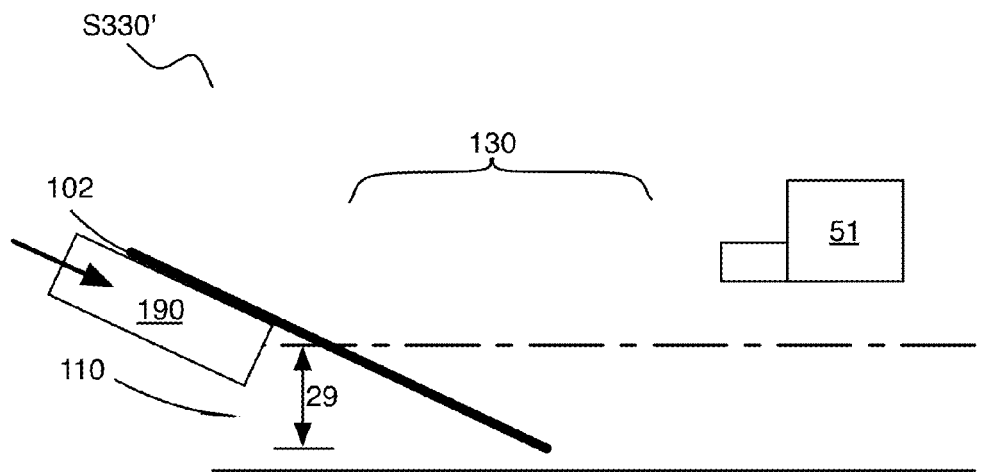
FIGS. 22A-22D depict phases of an example workflow implemented by an embodiment of a system for mounting a section to a substrate and removing wrinkles from the section.
Figure 22B:
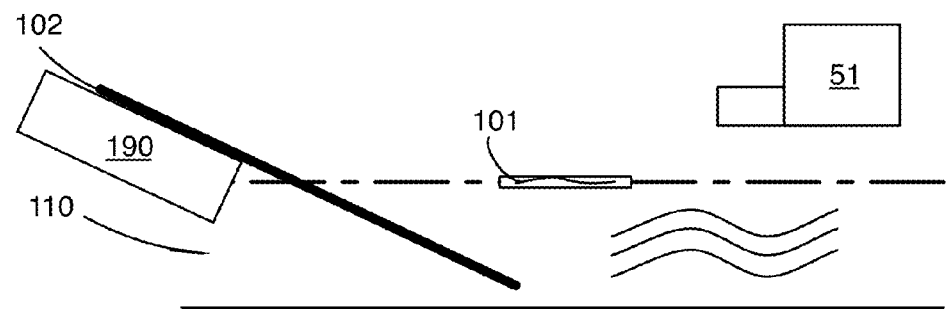
Figure 22C:
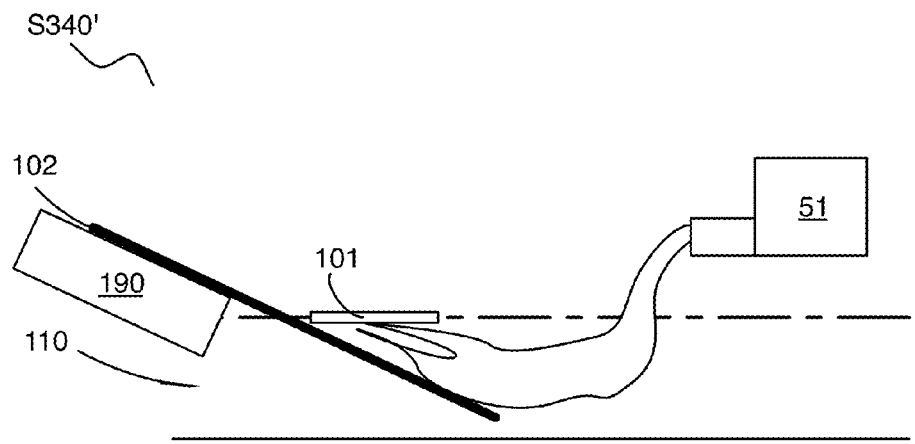
Figure 22D:
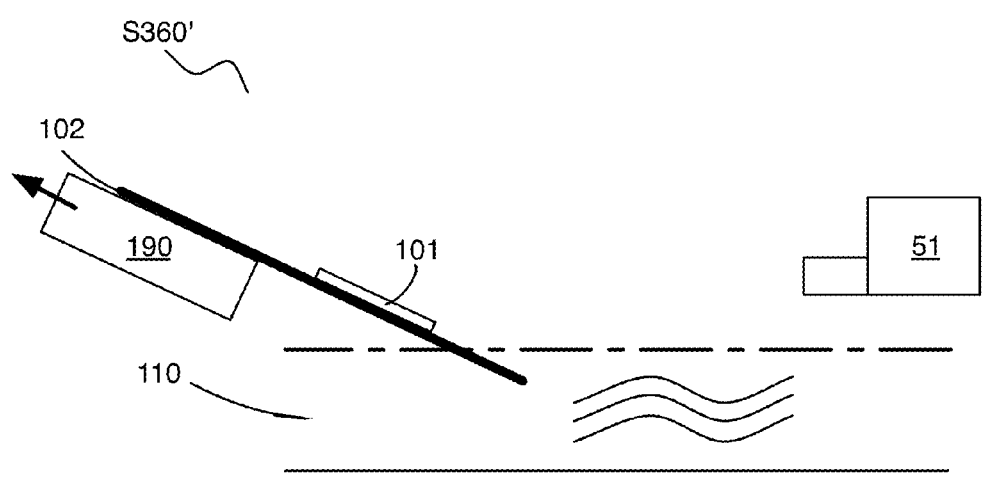

In one example operation, involving coordination between flow governed by the controller 168 of the pump 167, the wrinkle-removal module 50, and the substrate actuation module 190, the substrate actuation module 190 can be configured to transmit a substrate 102 to a desired fluid depth 29, as shown in FIG. 22A, within the section-mounting region 130 of the fluid channel 110. Then, a section 101 can be transmitted toward the section-mounting region 130 from the fluid channel inlet 110 after separation from a blade 3 of a microtome 104 of a sample-sectioning module 103, as shown in FIG. 22B, and the wrinkle-removal module 50 can inject a volume of high-temperature fluid toward the section 101 to remove wrinkles, as shown in FIG. 22C. Flow from the fluid channel inlet 120 can then be increased to facilitate delivery of the section 101 onto the substrate 102 as the substrate 102 is retracted from the section-mounting region 130 by the substrate actuation module 190, as shown in FIG. 22D. In variations involving mounting of multiple sections onto a single substrate 102, the above example can be repeated multiple times, with the substrate 102 delivered into the section-mounting region 130 of the fluid channel 110 at successively decreasing depths for each section 101 mounted to the substrate 102. Variations of the example can, however, involve any other suitable workflow.

1.5 System—Additional Elements and Alternative Configurations

Variations of the system 100 can alternatively omit any of the above described elements in order to provide simplified variations of the system 100. For instance, one variation of the system 100 can include a reservoir 150 comprising fluid and configured to receive a section 101 at a surface of fluid in the reservoir 150; and a wrinkle removal module 50 configured proximal to the section within the reservoir. In this simplified variation, the wrinkle removal module 50 can facilitate expansion of the section using one or more mechanisms as described above, and a human technician or other entity can mount the expanded section onto an imaging substrate manually or automatically. Variations of the above embodiments can further include any other suitable elements configured to facilitate mounting of a section onto an imaging substrate. For instance, a variation of the system 100 can include a tracking module configured to track a position of a section, and to facilitate wrinkle-removal within the section at any desired position in coordination with the tracking module. The system 100 can, however, omit and/or incorporate any other suitable element(s), or have alternative configurations, some of which are described below.

Figure 23:
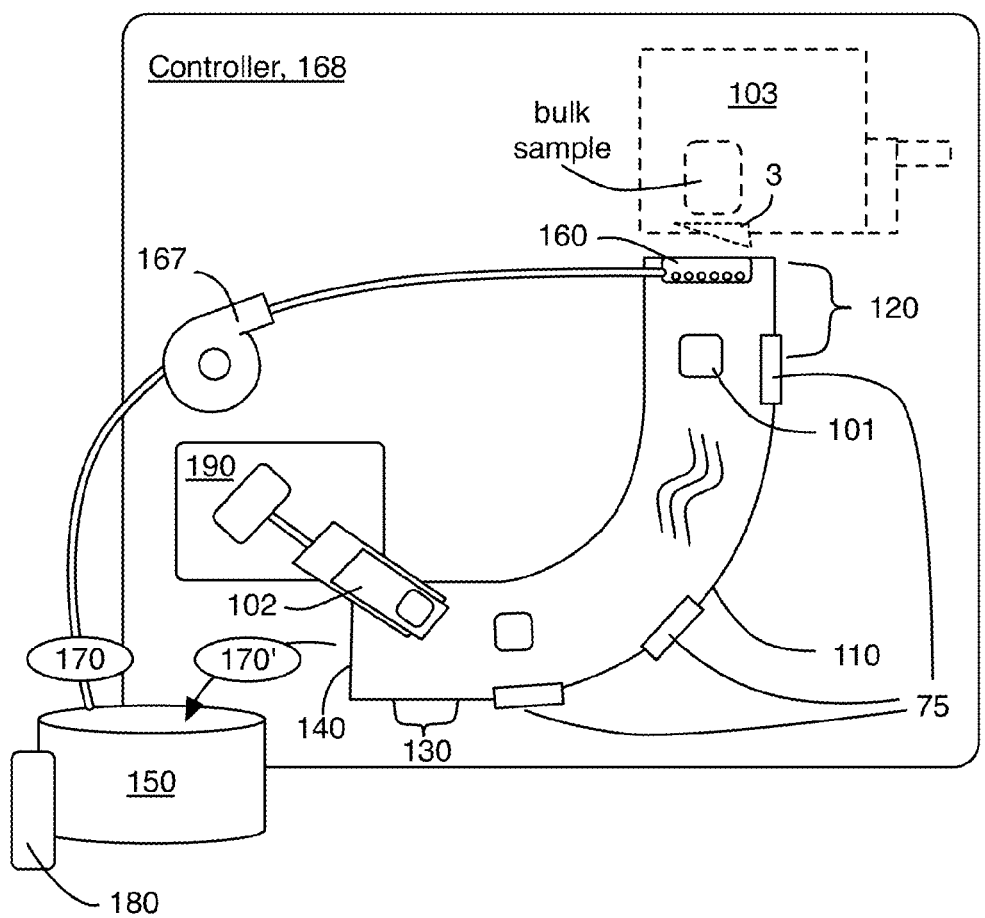
FIG. 23 depicts an embodiment of a system for mounting a section to a substrate.

In one variation of the system 100, one or more sensors 75 can be placed along the fluid channel 110 to enable detection of sections 101 as they pass, as shown in FIG. 23. The sensors can operate using any one or more of: infrared emitter-detector pairs, capacitive sensing, light contrast detection, image processing, and any other suitable mechanism to detect the presence, type, shape, and/or condition of a section 101 being transmitted through the fluid channel 110. Such sensors can function to facilitate appropriate timing of flow modulation for placement of a section 101 onto a substrate 102, as governed by a controller 168 of a pump 167 of the system 100. Such sensors can additionally or alternatively enable detection of the presence or absence of fluid in the fluid channel 110, a velocity of a section 101 as it is transmitted within the fluid channel 110, physical parameters of (e.g., dimensions of, damage to, etc.) a section 101 within the fluid channel 110, and any other suitable parameters. Such sensors can additionally or alternatively be used for subsequent, automated and/or manual, decision-making processes to adjust system performance, enable sorting of section, enable labeling or tagging of substrates with relevant information, and/or flagging conditions requiring operator intervention. The sensors can be mounted at an underside surface of the fluid channel 110 and configured to detect overhead passing sections (e.g., by way of transparent windows through the base surface of the fluid channel 110), or can additionally or alternatively be mounted above the fluid channel 110 and configured to detect sections passing below.

Figure 24:
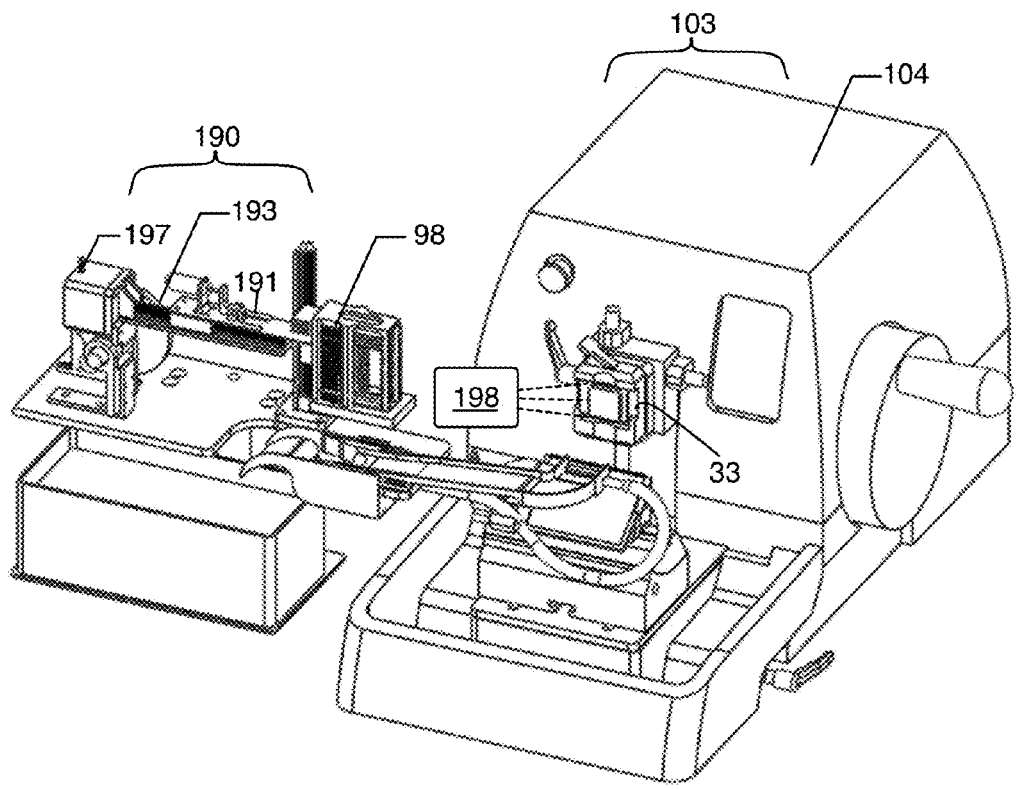
FIG. 24 depicts alternative examples of elements in an embodiment of a system for mounting a section to a substrate.

To automate management of substrates for rapid exchange of substrates with mounted sections and empty substrates, a rail 193 of the substrate actuation module 190 can be mounted on a pivoting element 197, as shown in FIG. 24. As such, the substrate actuation module 190, with a gripper 191 mounted to a rail 193 can form a robotic arm that can be used for retrieving and replacing mounted substrates, for submerging substrates at the section-mounting region 130 during section placement, and for retraction to different positions for placement of multiple sections. To facilitate automated retrieval and replacement, the substrate actuation module 193 can interface with a substrate rack 98 (e.g., rack of imaging slides) having a set of slots (e.g., parallel slots, radially oriented slots, etc.) configured to hold substrates for retrieval and replacement. Substrate manipulation by the system 100 can, however, be automated in any other suitable manner.

Figure 25:
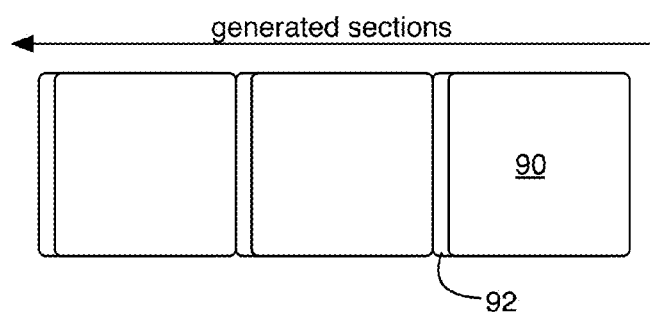
FIG. 25 depicts portions of adjoined sections in an embodiment of a system for mounting a section to a substrate.

To facilitate separation of adjoining sections produced by a sample sectioning module 103, the system 100 can include elements that apply a treatment to the top or bottom of an embedded tissue section to create dissimilar materials at a section-section junction, thereby reducing the tendency of sections to wrinkle or form ribbons during processing. As shown in FIG. 25, the embedding medium 90 can comprise wax, and treatment 92 can comprise a quick-setting enamel applied to bottoms of sections 101 to prevent formation of ribbons or wrinkling.

In some variations, the microtome 104 of a sample sectioning module 103 interfacing with the system 100 can comprise a temperature-regulated chuck 33, as shown in FIG. 24, that functions to maintain a bulk embedded sample at a desired temperature for sectioning. The temperature-regulated chuck 33 can also allow for consistent production of high-quality sections even if the bulk embedded sample is left within the chuck 33 for extended periods, such as when serial sectioning.

In some variations, the system 100 can include an atomizer 198 or other element, as shown in FIG. 24, configured to spray fluid over a sample to hydrate the bulk sample while it is being sectioned by the sample sectioning module 103. The atomizer 198 can thus prevent the need for an operator to periodically remove, hydrate, and replace a sample during sectioning of specific types of tissues that are susceptible to dehydration and flaking during sectioning. Additionally or alternatively, the system 100 can include a permeable material (e.g., sponge, fabric, etc.), saturated with a hydrating fluid and configured to contact the bulk sample (e.g., by providing relative motion between the bulk sample and the permeable material), in order to prevent drying of the bulk sample. Hydration of the bulk sample to improve sample processing can, however, be performed in any other suitable manner.

In some variations, the system 100 can include a laser-etching device that functions to label substrates as they are mounted with sections, thus further reducing a need for operator intervention in substrate labeling. The laser-etching device can further function to reduce a possibility of mis-matching substrate-mounted sections with their corresponding source embedded samples. The laser-etching device can be integrated with an informational technology (IT) system of a laboratory or clinic where the system 100 is in use.

In some variations, the system 100 can include an anti-static ionizing device that functions to ensure that each section 101 is electrostatically neutral at certain phases of processing. The anti-static ionizing device can minimize risk of electrostatic attraction or repelling of a cut section 101 toward a sidewall or other portion of the fluid channel 110 in a manner that could hinder mounting of the section to a substrate.

In some variations, the system 100 can include a kinetic sensor coupled to a blade 3 and/or sample mounting chuck of the sample sectioning module 103 that functions to sense acceleration, vibration, and/or any other kind of feedback that could be used to automatically adjust cutting motion of the sample sectioning module 103. The kinetic sensor can thus function to reduce operator interaction and improve automation in the system 100.

Figure 26:
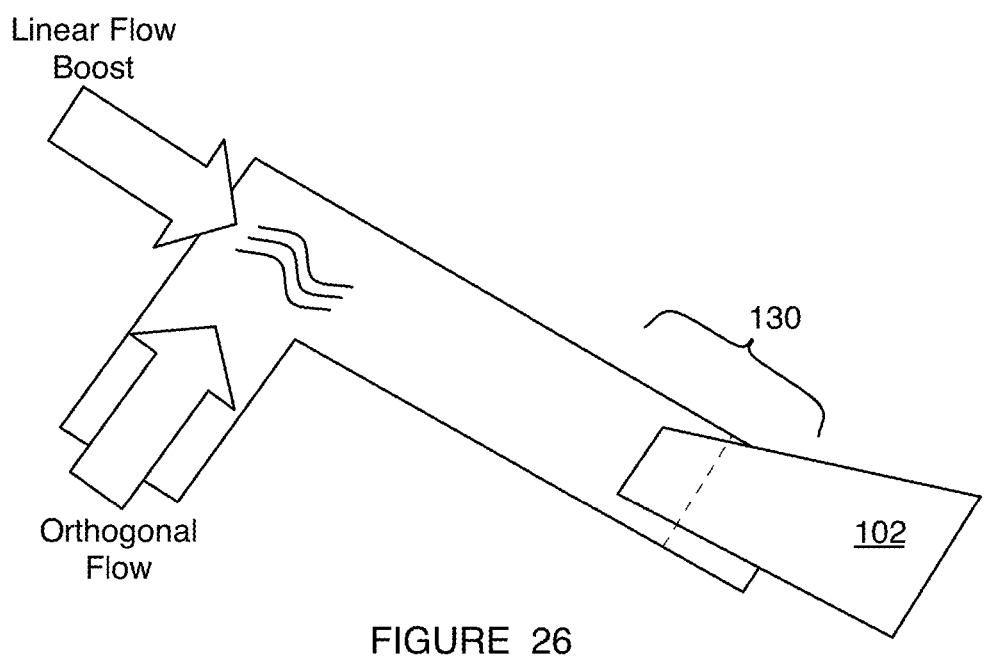
FIG. 26 depicts an alternative variation of a fluid channel in an embodiment of system for mounting a section to a substrate.

In one alternative configuration, sections can be transmitted to a substrate from a path that is perpendicular to that described in the embodiments and variations above, which allows for a condensed fluid path. In another alternative configuration, as shown in FIG. 26, a linear flow boost (i.e., a burst of fluid flow) can be used to introduce flow around a submerged substrate 102 at the section-mounting region 130 to produce consistent section placement upon a substrate 102.

The system 100 can, however, include any other suitable elements configured to facilitate mounting of one or more sections onto a substrate. Furthermore, as a person skilled in the art will recognize from the previous detailed description and from the figures and claims, modifications and changes can be made to the system 100 without departing from the scope of the system 100.

2. Method

Figure 27:
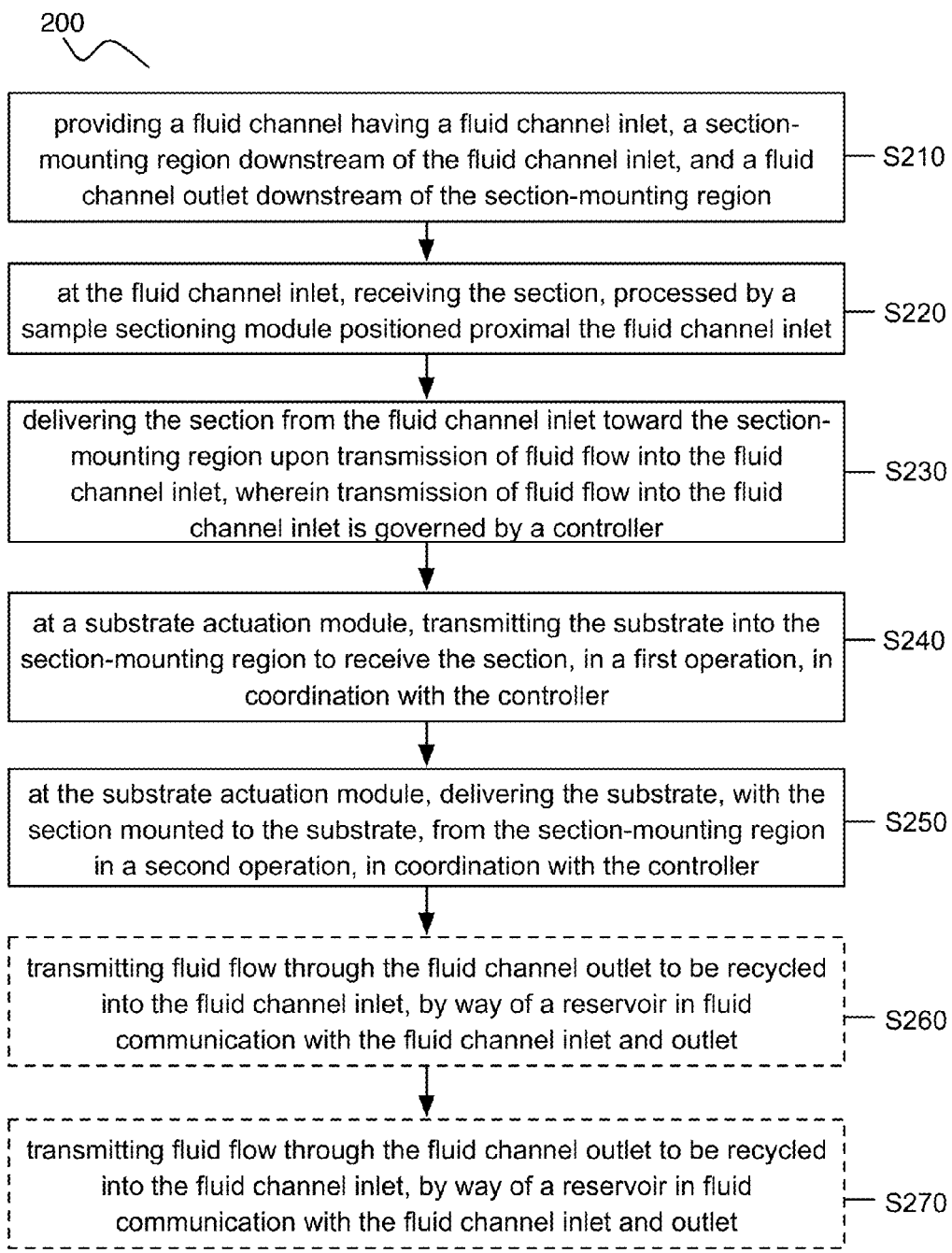
FIG. 27 depicts a flow chart of an embodiment of a method for mounting a section to a substrate.
Figure 28:
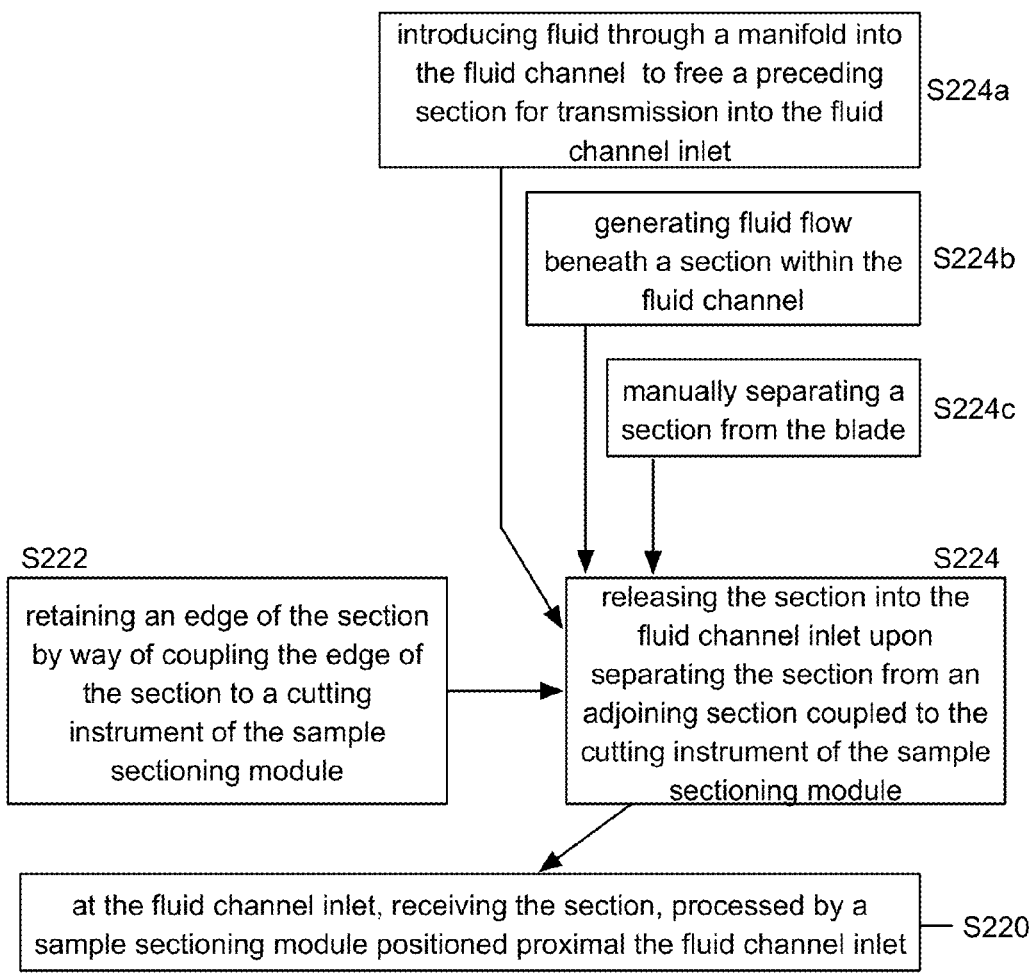
FIG. 28 depicts variations of a portion of an embodiment of a method for mounting a section to a substrate.

As shown in FIG. 27, an embodiment of a method 100 for coupling a section to a substrate comprises: providing a fluid channel having a fluid channel inlet, a section-mounting region downstream of the fluid channel inlet, and a fluid channel outlet downstream of the section-mounting region S210; at the fluid channel inlet, receiving the section, processed by a sample sectioning module positioned proximal the fluid channel inlet S220; delivering the section from the fluid channel inlet toward the section-mounting region upon transmission of fluid flow into the fluid channel inlet, wherein transmission of fluid flow into the fluid channel inlet is governed by a controller S230; at a substrate actuation module, transmitting the substrate into the section-mounting region to receive the section, in a first operation, in coordination with the controller S240; and at the substrate actuation module, delivering the substrate, with the section mounted to the substrate, from the section-mounting region in a second operation, in coordination with the controller S250. In some embodiments, the method 200 can include any one or more of: transmitting fluid flow through the fluid channel outlet to be recycled into the fluid channel inlet, by way of a reservoir in fluid communication with the fluid channel inlet and outlet S260; and at a wrinkle-removal module proximal to the section-mounting region, transmitting heat toward the section, thereby mitigating wrinkling of the section at the substrate S270.

The method 200 functions to automate processing of sections (e.g., histological specimen sections, biological sections, etc.) in a manner that consistently generates high-quality mounted sections, with minimal or no effort from a human technician. As such, the method 200 can significantly reduce labor-intensive aspects of mounting sections to substrates. The method 200 is preferably implemented by at least a portion of the system 100 described in Section 1 above; however, the method 200 can additionally or alternatively be implemented using any other suitable system(s).

Block S210 recites: providing a fluid channel having a fluid channel inlet, a section-mounting region downstream of the fluid channel inlet, and a fluid channel outlet downstream of the section-mounting region. Block S210 functions to provide a fluid conveyer that can be used to drive a section for mounting at a substrate. Block S210 is preferably implemented using an embodiment of the system 100 described above, and more specifically, using embodiments, variations, and/or examples of the fluid channel 110, fluid channel inlet 120, section-mounting region 130, and fluid channel outlet 140 described above; however, Block S210 can alternatively be implemented using any other suitable system 100 that provides a fluid path, with control of fluid flow parameters for automatically mounting histological sections to one or more substrates.

Block S220 recites: at the fluid channel inlet, receiving the section, processed by a sample sectioning module positioned proximal the fluid channel inlet. Block S220 functions to initiate sample reception within the fluid channel, such that the sample can be transmitted to downstream portions for manipulation (e.g., positioning, de-wrinkling) and mounting at a substrate. In Block S220, the section is preferably received from a bulk embedded sample processed by a sample sectioning module (e.g., comprising a microtome with a blade proximal the fluid channel inlet); however, the section can alternatively be received in Block S220 in any other suitable manner. In some variations, Block S220 can include one or more of: retaining an edge of the section by way of coupling the edge of the section to a cutting instrument of the sample sectioning module S222; and releasing the section into the fluid channel inlet upon separating the section from an adjoining section coupled to the cutting instrument of the sample sectioning module S224. Block S224, as described above, can include any one or more of: introducing fluid through a manifold into the fluid channel (e.g., at an angle γ) to free a preceding section for transmission into the fluid channel inlet S224a; generating fluid flow beneath a section within the fluid channel S224b, such that a shear force induced at a junction between sections provides separation; manually separating a section from the blade (e.g., using forceps) S224c; implementing an elevated floor of the fluid channel inlet, immediately downstream of the manifold, to cause fluid to be drawn away from the blade as it is delivered into the fluid channel; using a separation device (e.g., a paddle, a chuck, etc.), as shown in FIGS. 4A-4C, thereby providing a mechanical force that separates adjoined sections; and using any other suitable method of separating adjoining sections without damaging sections. Block S220 can, however, include any other suitable steps for transmitting a section that has been cut from a bulk embedded sample into the fluid channel inlet.

Figure 29:
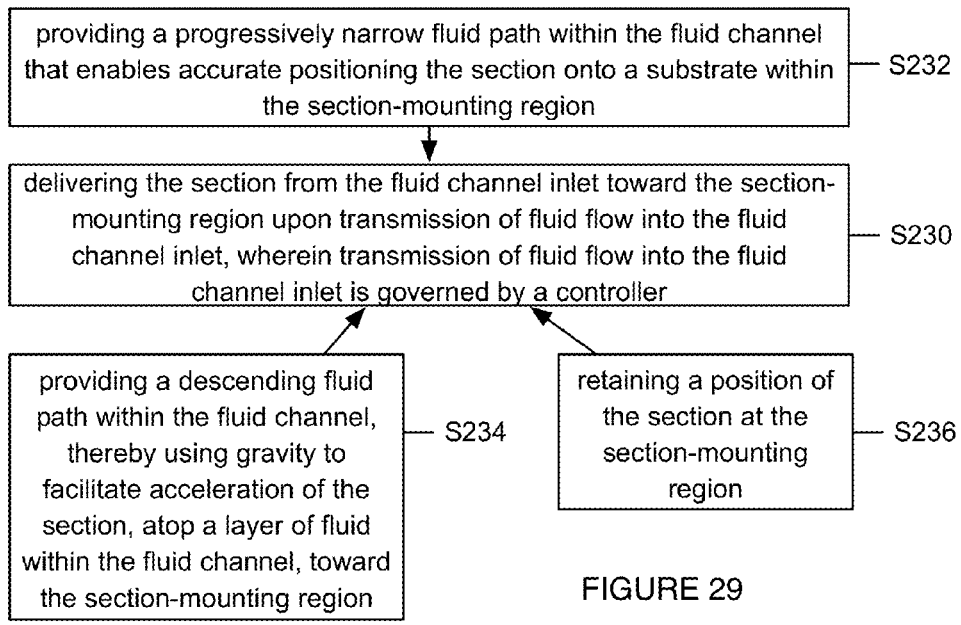
FIG. 29 depicts variations of a portion of an embodiment of a method for mounting a section to a substrate.

Block S230 recites: delivering the section from the fluid channel inlet toward the section-mounting region upon transmission of fluid flow into the fluid channel inlet, wherein transmission of fluid flow into the fluid channel inlet is governed by a controller. Block S230 functions to drive a section, floating atop fluid within the fluid channel, toward the section-mounting region of the fluid channel upon transmission of fluid through a manifold in fluid communication with the fluid channel inlet. Block S230 is preferably implemented using embodiments, variations, and/or examples of the fluid channel 110, the pump 167, the controller 168, and the manifold 160 described in Section 1 above; however, Block S230 can additionally or alternatively be implemented using any other suitable system or element(s). As shown in FIG. 29, delivering the section toward the section-mounting region in Block S230 can thus include any one or more of: providing a progressively narrow fluid path within the fluid channel that enables accurate positioning the section onto a substrate within the section-mounting region S232; providing a descending fluid path within the fluid channel, thereby using gravity to facilitate acceleration of the section, atop a layer of fluid within the fluid channel, toward the section-mounting region S234; retaining a position of the section at the section-mounting region S236 (e.g., upon modulation of fluid flow parameters); and using any other suitable block that enables accurate placement of a section at a substrate, in a repeatable manner.

Figure 30:
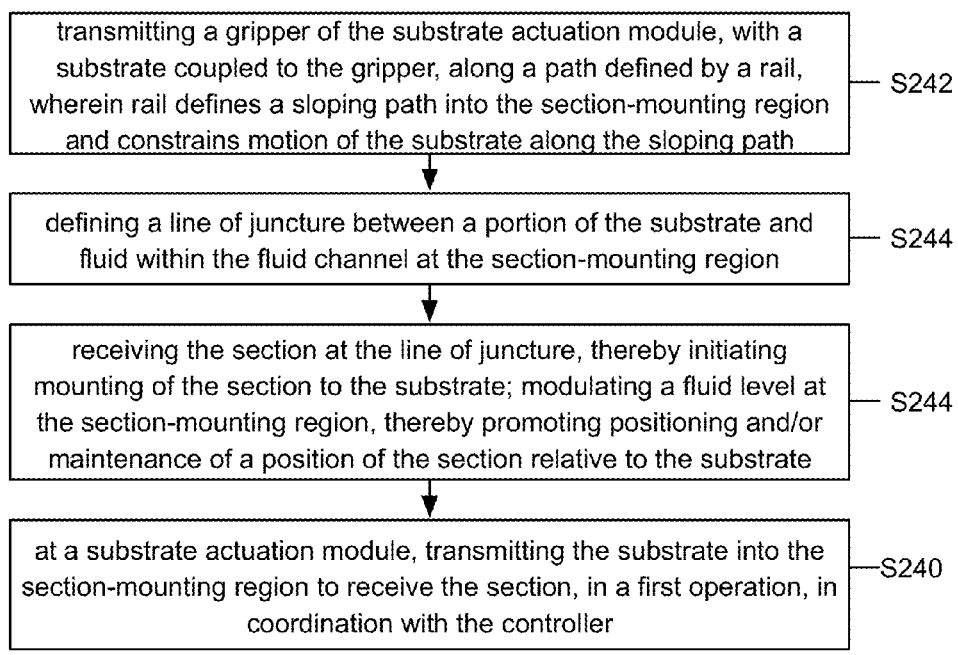
FIG. 30 depicts variations of a portion of an embodiment of a method for mounting a section to a substrate.

Block S240 recites: at a substrate actuation module, transmitting the substrate into the section-mounting region to receive the section, in a first operation, in coordination with the controller. Block S240 functions to position a substrate at a desired depth and/or with a desired angle relative to a base surface of the fluid channel at the section-mounting region, which allows accurate positioning and mounting of the section to the substrate. Block S240 is preferably implemented using an embodiment, variation, or example of the substrate actuation module 190, substrate 102, and section-mounting region 130 described in Section 1 above; however, Block S240 can alternatively be implemented using any other suitable system or element(s). In variations, as shown in FIG. 30, Block S240 can include any one or more of: transmitting a gripper of the substrate actuation module, with a substrate coupled to the gripper, along a path defined by a rail, wherein rail defines a sloping path into the section-mounting region and constrains motion of the substrate along the sloping path S242; defining a line of juncture between a portion of the substrate and fluid within the fluid channel at the section-mounting region S244; receiving the section at the line of juncture, thereby initiating mounting of the section to the substrate; modulating a fluid level at the section-mounting region, thereby promoting positioning and/or maintenance of a position of the section relative to the substrate S246; and performing any other suitable action that facilitates initial coupling of the section to the substrate. Block S240 is thus preferably performed in coordination with modulation of flow parameters within the fluid channel by the controller, such that fluid parameters (e.g., flow velocity, flow acceleration, fluid level, etc.) for promoting accurate and repeatable coupling of a section to the substrate is substantially synchronized with motion of the substrate actuation module and coupled substrate.

Figure 31:
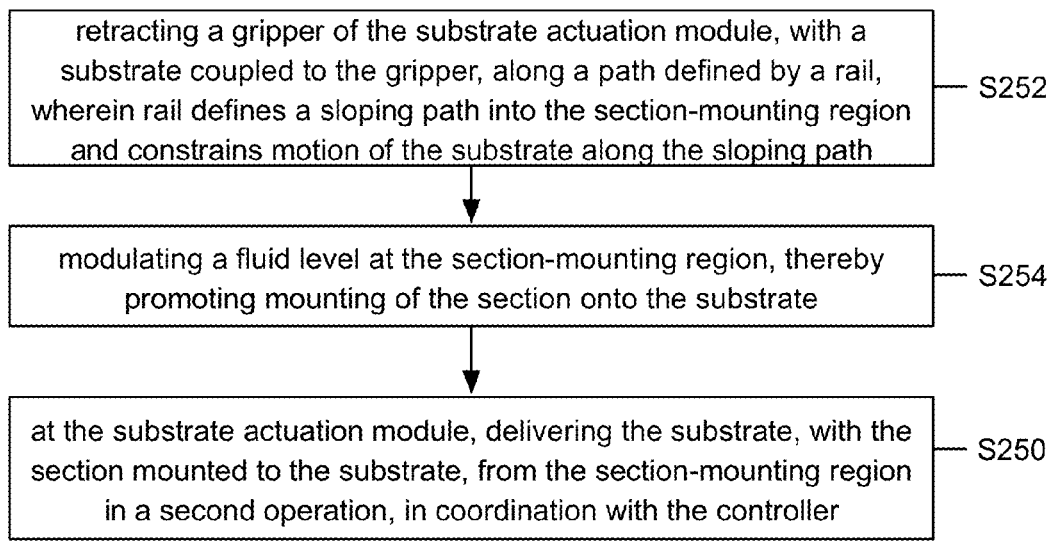
FIG. 31 depicts variations of a portion of an embodiment of a method for mounting a section to a substrate.
Figure 32:
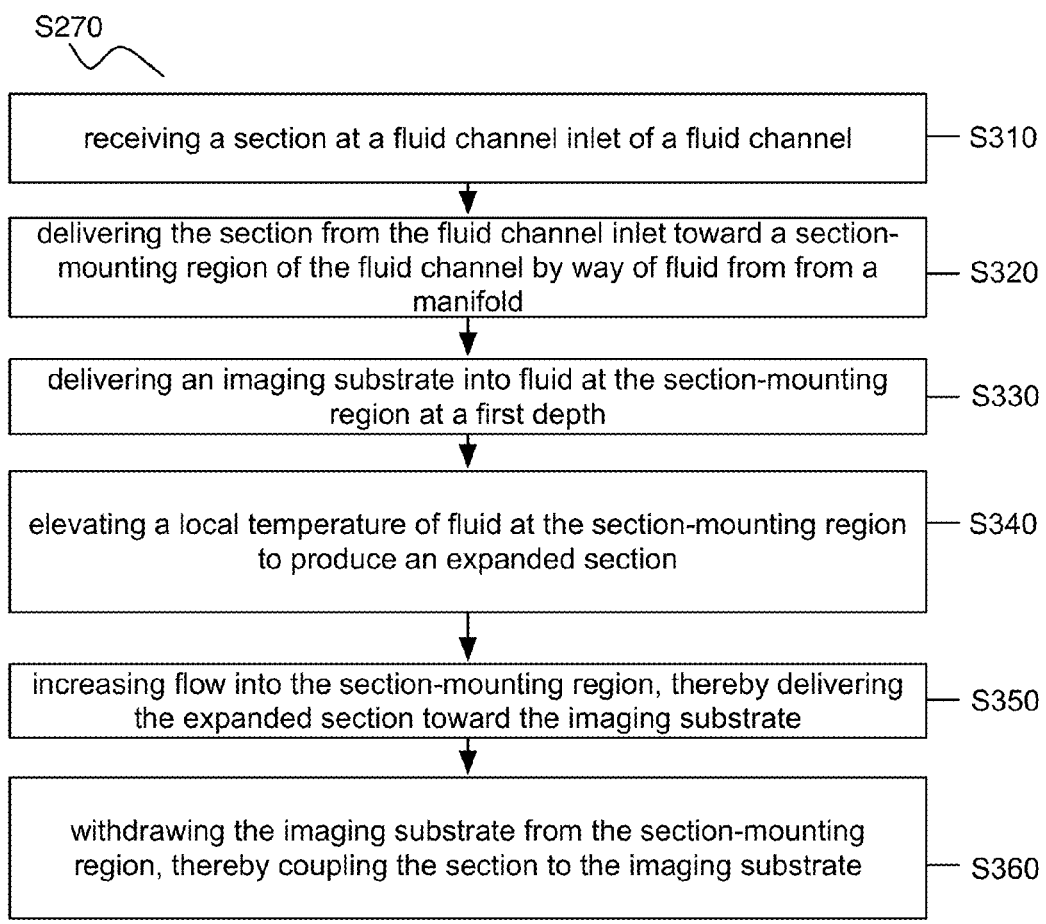
FIG. 32 depicts variations of a portion of an embodiment of a method for mounting a section to a substrate.

Block S250 recites: at the substrate actuation module, delivering the substrate, with the section mounted to the substrate, from the section-mounting region in a second operation, in coordination with the controller. Block S250 functions to retract a substrate from a position within the section-mounting region, with a section at least partially coupled to the substrate, which allows the section to gradually be fully mounted to the substrate. Block S250 is preferably implemented using an embodiment, variation, or example of the substrate actuation module 190, substrate 102, and section-mounting region 130 described in Section 1 above; however, Block S250 can alternatively be implemented using any other suitable system or element(s). In variations, as shown in FIG. 31, Block S250 can include any one or more of: retracting a gripper of the substrate actuation module, with a substrate coupled to the gripper, along a path defined by a rail, wherein rail defines a sloping path into the section-mounting region and constrains motion of the substrate along the sloping path S252; modulating a fluid level at the section-mounting region, thereby promoting mounting of the section onto the substrate S254 by producing an adhesion force between the section and the substrate; and performing any other suitable action that facilitates initial coupling of the section to the substrate. Block S250 is thus preferably performed in coordination with modulation of flow parameters within the fluid channel by the controller, such that fluid parameters (e.g., flow velocity, flow acceleration, fluid level, etc.) for promoting mounting of a section to the substrate in an accurate and repeatable manner is substantially synchronized with motion of the substrate actuation module and coupled substrate.

In some variations, Blocks S240 and S250 can be iteratively repeated for mounting of multiple sections to a single substrate, wherein a substrate is delivered to progressively decreasing depths within the section-mounting region to enable reception of multiple sections at desired positions along the substrate. An example workflow of mounting multiple sections to a single substrate is shown in FIGS. 13A-13C.

In some variations, the method 200 can include Block S260, which recites: transmitting fluid flow through the fluid channel outlet to be recycled into the fluid channel inlet, by way of a reservoir in fluid communication with the fluid channel inlet and the fluid channel outlet. Block S260 functions minimize wasting of fluid by the system, by using recirculated fluid to process samples. Block S260 is preferably implemented using embodiments, variations, and/or examples of the fluid channel outlet 140, the reservoir 150, the pump 167, the controller 168, the filter 170, and the manifold 160 described in Section 1 above; however, Block S260 can alternatively be implemented using any other suitable system or elements. Block S260 preferably includes providing a flow path from the fluid channel to the reservoir, by way of the fluid channel outlet, and can additionally or alternatively include one or more of: filtering fluid at least at one of the fluid channel outlet, the reservoir, the pump, and the manifold S262, thereby removing undesired substances prior to recirculation of fluid through the system; modulating a temperature of fluid at least at one of the reservoir, the manifold, and a portion of the fluid channel S264; introducing an additive for surface tension modulation along with fluid from the reservoir, during recirculation S266; and any other suitable step that facilitates recycling of fluid in the system with minimal operator involvement.

In some variations, the method 200 can additionally or alternatively include Block S270, which recites: at a wrinkle-removal module proximal to the section-mounting region, transmitting heat toward the section, thereby mitigating wrinkling of the section at the substrate. Block S270 functions to produce high-quality mounted sections, substantially free of wrinkling, upon transmitting heat to sections within the system 100 at desired stages of processing. Block S270 is preferably implemented using an embodiment, variation, or example of the wrinkle-removal module 50 described in Section 1 above, whereby transmitting heat toward the section can include any one or more of: injecting fluid with a desired temperature toward a section at the section-mounting region S272 (e.g., from underneath the section, from above the section, upstream of the section, downstream of the section, from sidewalls surrounding the section, etc); convectively transferring heat toward at least one surface of a section S274; heating a substrate to which a section is mounted or is intended to be mounted S276; and using any other suitable mechanism of heat transfer to de-wrinkle a section.

In one variation, as shown in FIGS. 32 and 22A-22D, Block S270 can include receiving the section at a fluid channel inlet of a fluid channel S310; delivering the section from the fluid channel inlet toward a section-mounting region of the fluid channel by way of fluid flow from a manifold proximal to the fluid channel inlet S320; delivering an imaging substrate into fluid at the section-mounting region at a first depth S330 by way of a substrate actuation module; elevating a local temperature of fluid at the section-mounting region in coordination with delivery of the section into the section-mounting region S340 to produce an expanded section; increasing flow into the section-mounting region, thereby delivering the expanded section toward the imaging substrate S350; and withdrawing the imaging substrate from the section-mounting region by way of the gripper module S360, thereby coupling the section to the imaging substrate.

However, Block S270 can alternatively include removing wrinkles from a section prior to, during, or after mounting, using any other suitable apparatus. For instance, Block S270 can include preventing wrinkling of a section by modulating a viscosity parameter or surface tension parameter of the fluid conveying the section to the section-mounting region, or by using acoustic vibrations to remove wrinkles from a section.

The method 200 can, however, include any other suitable blocks or steps configured to facilitate mounting of one or more sections onto a substrate in an automated or semi-automated manner. In one variation, the method 200 can include detecting, at a sensor system, one or more of: a section passing through a portion of the fluid channel, presence or absence of fluid in the fluid channel, a velocity of the section as it is transmitted within the fluid channel, physical parameters of (e.g., dimensions of, damage to, etc.) the section within the fluid channel 110, and any other suitable parameters. In related variations, the method 100 can include timing flow modulation for placement of the section onto the substrate in response to signals generated by the sensor system.

In variations, the method 200 can additionally or alternatively include one or more of: applying a treatment to a portion of a bulk embedded sample used to generate the section, in order to prevent section wrinkling; automatically regulating a temperature of the bulk embedded sample; automatically spraying fluid over a portion of the bulk embedded sample to hydrate the sample while it is being sectioned by a sample sectioning module; with a laser-etching device, automatically labeling substrates as they are mounted with sections; with an anti-static ionizing device, ensuring that the section is at an electrostatically neutral state during processing; based upon signals from a kinetic sensor coupled to the sample-sectioning module, automatically modulating sectioning parameters to improve section quality; and any other suitable step that automates sample processing and/or improves quality of samples.

Variations of the system 100 and method 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention as defined in the following claims.

We claim:

1. A system for mounting a section onto a substrate, the system comprising:
    A blade that, during operation, generates the section from a bulk sample retained within a sample sectioning module;
    a fluid channel positioned at an output region of the blade and including:
        a fluid channel inlet that receives the section from the blade, and
        a section-mounting region downstream of the fluid channel inlet; and
        a fluid channel outlet;
    a reservoir in fluid communication with the fluid channel outlet; and
    a manifold, fluidly coupled to the reservoir, that delivers fluid from the reservoir to the fluid channel inlet, thereby transmitting fluid flow that drives delivery of the section from the fluid channel inlet toward the section-mounting region.

2. The system of claim 1, further comprising a filter, fluidly configured between the fluid channel outlet and the manifold, that prevents undesired substances from flowing into the fluid channel inlet.

3. The system of claim 1, wherein the fluid channel inlet includes a junction at an upstream portion of the fluid channel inlet, the junction defining a region with a raised floor within the fluid channel that facilitates acceleration of the section from the fluid channel inlet toward the section-mounting region.

4. The system of claim 1, wherein the section-mounting region comprises a base surface having a contoured surface submerged below a fluid line of fluid within the section-mounting region, that facilitates mounting of the section the substrate, and wherein the section-mounting region is coupled to the fluid channel inlet by a chute that provides downhill flow for acceleration of the section from the fluid channel inlet toward the section-mounting region.

5. The system of claim 1, wherein the reservoir comprises a temperature regulating module in contact with fluid from the reservoir, that adjusts a temperature of fluid from the reservoir prior to transmission into the fluid channel.

6. The system of claim 1, wherein a width dimension of the fluid channel narrows from the fluid channel inlet to the section-mounting region, thereby facilitating alignment of the section onto the substrate.

7. The system of claim 1, further comprising a substrate actuation module proximal the section-mounting region that transmits the substrate into the section-mounting region in a first operation, and delivers the substrate from the section-mounting region, with the section mounted to the substrate, in a second operation.

8. The system of claim 7, further comprising a pump coupled to the reservoir and governed by a controller, wherein the controller governs fluid flow from the reservoir into the fluid channel inlet and wherein the substrate actuation module coordinates with the controller in mounting the section to the substrate.

9. The system of claim 7, wherein the substrate actuation module comprises a grip configured to couple to a surface of the substrate, a rail along which the grip translates, and an actuator configured to provide motion of the grip along the rail.

10. The system of claim 7, wherein the substrate actuation module is configured to repeatably retract and transmit the substrate into the section-mounting region for mounting of a set of sections, generated from the bulk sample, to the substrate.

11. The system of claim 1, wherein the manifold comprises a set of openings that direct fluid at an angle relative to a base surface of the fluid channel inlet, thereby providing a force that separates the section from the blade.

12. The system of claim 1, further including a wrinkle removal module configured to transmit heat toward the section at the section-mounting region, thereby removing wrinkles from the section.

13. A method for mounting a section onto a substrate, the method comprising:
  providing a fluid channel having a fluid channel inlet and a section-mounting region downstream of the fluid channel inlet;
  receiving the section, from a blade that generates the section from a bulk sample, into the fluid channel inlet;
  delivering the section from the fluid channel inlet toward the section-mounting region upon transmission of fluid flow into the fluid channel inlet, wherein transmission of fluid flow is governed by a controller;
  at a substrate actuation module, transmitting the substrate into the section-mounting region to receive the section, in a first operation, in coordination with the controller, thereby placing the section onto the substrate.

14. The method of claim 13, wherein receiving the section at the fluid channel inlet comprises retaining an edge of the section at the blade, and releasing the section into the fluid channel inlet upon delivering fluid flow, through a manifold, that separates the section from an adjoining section processed by the blade.

15. The method of claim 13, further comprising: at the substrate actuation module, delivering the substrate, with the section mounted to the substrate, from the section-mounting region in a second operation, in coordination with the controller.

16. The method of claim 15, wherein delivering the substrate from the section-mounting region, comprises retracting a grip of the substrate actuation module, with a substrate coupled to the grip; and producing an adhesion force between the section and the substrate during retraction of the substrate from the section-mounting region.

17. The method of claim 15, wherein transmitting the substrate into the section-mounting region comprises providing an interface between the substrate and fluid within the section-mounting region, receiving the section at the interface, and modulating a level of fluid within the section-mounting region, thereby promoting positioning of the section at the substrate.

18. The method of claim 13, wherein delivering the section from the fluid channel inlet toward the section mounting region comprises providing a descending fluid path within the fluid channel, thereby using gravity to facilitate acceleration of the section, positioned at a layer of fluid within the fluid channel, toward the section-mounting region.

19. The method of claim 13, wherein delivering the section from the fluid channel inlet toward the section mounting region comprises providing a progressively narrow fluid path within the fluid channel that enables accurate positioning the section onto the substrate within the section-mounting region.

20. The method of claim 13, further comprising transmitting fluid flow through an outlet of the fluid channel into a reservoir in fluid communication with the fluid channel inlet, and transmitting fluid flow from the reservoir into the fluid channel inlet, thereby delivering the section from the blade and into the fluid channel inlet.

* * * * *